US008338614B2

(12) United States Patent
McGaughey et al.

(10) Patent No.: US 8,338,614 B2
(45) Date of Patent: *Dec. 25, 2012

(54) TERTIARY CARBINAMINES HAVING SUBSTITUTED HETEROCYCLES WHICH ARE ACTIVE AS β-SECRETASE INHIBITORS FOR THE TREATMENT OF ALZHEIMER'S DISEASE

(75) Inventors: Georgia B. McGaughey, Harleysville, PA (US); Philippe G. Nantermet, Lansdale, PA (US); Hemaka A. Rajapakse, Wyncote, PA (US); Shaun R. Stauffer, Schwenksville, PA (US)

(73) Assignee: Merck, Sharp & Dohme Corp., Rahway, NJ (US)

( * ) Notice: Subject to any disclaimer, the term of this patent is extended or adjusted under 35 U.S.C. 154(b) by 124 days.

This patent is subject to a terminal disclaimer.

(21) Appl. No.: 11/795,190

(22) PCT Filed: Jan. 13, 2006

(86) PCT No.: PCT/US2006/001367
§ 371 (c)(1),
(2), (4) Date: Jul. 12, 2007

(87) PCT Pub. No.: WO2006/078577
PCT Pub. Date: Jul. 27, 2006

(65) Prior Publication Data
US 2008/0139538 A1    Jun. 12, 2008

Related U.S. Application Data

(60) Provisional application No. 60/644,924, filed on Jan. 19, 2005, provisional application No. 60/652,421, filed on Feb. 11, 2005.

(51) Int. Cl.
*C07D 271/10* (2006.01)
*C07D 271/113* (2006.01)
*C07D 271/107* (2006.01)
*C07D 487/02* (2006.01)
*C07D 237/26* (2006.01)
*C07D 413/06* (2006.01)
*C07D 401/06* (2006.01)
*C07D 213/02* (2006.01)
*C07D 243/14* (2006.01)
*A61K 31/519* (2006.01)
*A61K 31/141* (2006.01)
*A61K 31/495* (2006.01)
*A61K 31/535* (2006.01)
*A61K 31/55* (2006.01)
*A61K 31/44* (2006.01)

(52) U.S. Cl. ........ 548/131; 548/132; 548/133; 544/263; 544/235; 544/138; 540/569; 546/193; 546/125; 514/259.31; 514/364; 514/248; 514/235.8; 514/221; 514/304

(58) Field of Classification Search .................. 540/484; 544/140, 224; 546/112, 184; 548/250, 255, 548/262, 2, 300.1, 356.1, 400
See application file for complete search history.

(56) References Cited

U.S. PATENT DOCUMENTS

| | | | |
|---|---|---|---|
| 5,665,718 A | 9/1997 | Godel et al. | |
| 6,566,311 B1 | 5/2003 | Nalesnik | |
| 6,852,719 B2 | 2/2005 | Liu et al. | |
| 6,951,946 B2 | 10/2005 | Kolb et al. | |
| 7,115,652 B2 | 10/2006 | Yang | |
| 2003/0232875 A1* | 12/2003 | Bartlett et al. | 514/412 |
| 2004/0132782 A1 | 7/2004 | Yang et al. | |
| 2007/0244119 A1* | 10/2007 | Barrow et al. | 514/236.2 |
| 2007/0293497 A1* | 12/2007 | Nantermet et al. | 514/340 |
| 2008/0015233 A1* | 1/2008 | Barrow et al. | 514/340 |
| 2008/0153846 A1* | 6/2008 | Coburn et al. | 514/254.03 |

FOREIGN PATENT DOCUMENTS

| | | |
|---|---|---|
| WO | WO 02/20530 A | 3/2002 |
| WO | WO 2005/103020 | 11/2005 |
| WO | WO 2005/103043 | 11/2005 |
| WO | WO 2006/057945 | 6/2006 |
| WO | WO 2006/078577 | 7/2006 |

OTHER PUBLICATIONS

Barrett, D. G., Orally bioavailable small molecule ketoamide-based inhibitors of cathepsin K. Bio. Med. Chem. Lett., Feb. 2004, vol. 14, pp. 2543-2546.
Han, Y. Novel pyrazinone mono-amides as potent and reversible caspase-2 inhibitors. Bio. Med. Chem. Lett. Dec. 2004, vol. 15, pp. 1173-1180.
Helvetic Chimica Acta, vol. 61, No. 7, 1978, pp. 2419-2427; "230. Synthese von 1, 3,4-Oxadiazolen und 4,5-Dihydro-1,2,4-triazinen aus 3-Dimethylamino-2,2-dimethyl-2H-azirin and Carbohydraziden".
Magirus, F.; et. al.; Helvetica Chemica Acta, Basel, CH, vol. 76, No. 5; Jan. 1, 1993; pp. 1980-2003; "137. Umsetzung Von 3-Amino-2H-Azirinen Mit Salicylohydrazid".
Stanislav, Chaloupka; Heinz Heimgartner: vol. 31, No. 9, 1978, pp. 332-333; "Reaktionen von 3-Dimethylamino-2,2-dimethyl-2H-azirin mit aromatischen Carbonsaurehydraziden".
Database Crossfire Beilstein; Beilstein Institute Zur Forderung Der Wissenschaften, Franfurt Am Main, DE; XP002569252 Database accession No. 4610194 (BRN) *abstract* & Ashok Kumar, B.P. Jaju, S. Gurtu, J.N. Sinha, K. Shankar: Indian Journal of Chemistry, including Medicina Chemistry, vol. 27, Nos. 1-12, 1988; pp. 93-95.

* cited by examiner

*Primary Examiner* — Kamal Saeed
*Assistant Examiner* — Nyeemah A Grazier
(74) *Attorney, Agent, or Firm* — Keith D. MacMillan; Gerard M. Devlin

(57) ABSTRACT

The present invention is directed to tertiary carbinamine compounds having substituted heterocycles, which are inhibitors of the beta-secretase enzyme, and are useful in the treatment of diseases in which the beta-secretase enzyme is involved, such as Alzheimer's disease. The invention is also directed to pharmaceutical compositions comprising these compounds and the use of these compounds and compositions in the treatment of such diseases in which the beta-secretase enzyme is involved.

7 Claims, No Drawings

TERTIARY CARBINAMINES HAVING SUBSTITUTED HETEROCYCLES WHICH ARE ACTIVE AS β-SECRETASE INHIBITORS FOR THE TREATMENT OF ALZHEIMER'S DISEASE

CROSS-REFERENCE TO RELATED APPLICATIONS

This application claims priority under 35 U.S.C. §119 (e) of U.S. provisional applications Ser. Nos. 60/644,924, filed Jan. 19, 2005, and 60/652,421, filed Feb. 11, 2005.

REFERENCE TO JOINT RESEARCH AGREEMENT

This invention was made as a result of activities undertaken within the scope of a Joint Research Agreement between Merck & Co., Inc. and Sunesis Pharmaceuticals, Inc.

FIELD OF THE INVENTION

The invention is directed to a class of tertiary carbinamines having substituted heterocycles which are useful as inhibitors of the β-secretase enzyme, and to the treatment of diseases in which the β-secretase enzyme is involved, such as Alzheimer's Disease.

BACKGROUND OF THE INVENTION

Alzheimer's disease is characterized by the abnormal deposition of amyloid in the brain in the form of extra-cellular plaques and intra-cellular neurofibrillary tangles. The rate of amyloid accumulation is a combination of the rates of formation, aggregation and egress from the brain. It is generally accepted that the main constituent of amyloid plaques is the 4 kD amyloid protein (βA4, also referred to as Aββ-protein and βAP) which is a proteolytic product of a precursor protein of much larger size. The amyloid precursor protein (APP or AβPP) has a receptor-like structure with a large ectodomain, a membrane spanning region and a short cytoplasmic tail. The Aβ domain encompasses parts of both extra-cellular and transmembrane domains of APP, thus its release implies the existence of two distinct proteolytic events to generate its $NH_2$— and COOH-termini. At least two secretory mechanisms exist which release APP from the membrane and generate soluble, COOH-truncated forms of APP ($APP_s$). Proteases that release APP and its fragments from the membrane are termed "secretases." Most $APP_s$ is released by a putative α-secretase which cleaves within the Aβ protein to release α-$APP_s$ and precludes the release of intact Aβ. A minor portion of $APP_s$ is released by a β-secretase ("β-secretase"), which cleaves near the $NH_2$-terminus of APP and produces COOH-terminal fragments (CTFs) which contain the whole Aβ domain.

Thus, the activity of β-secretase or β-site amyloid precursor protein-cleaving enzyme ("BACE") leads to the abnormal cleavage of APP, production of Aβ, and accumulation of β amyloid plaques in the brain, which is characteristic of Alzheimer's disease (see R. N. Rosenberg, *Arch. Neurol.*, vol. 59, September 2002, pp. 1367-1368; H. Fukumoto et al, *Arch. Neurol.*, vol. 59, September 2002, pp. 1381-1389; J. T. Huse et al, *J. Biol. Chem.*, vol 277, No. 18, issue of May 3, 2002, pp. 16278-16284; K. C. Chen and W. J. Howe, *Biochem. Biophys. Res. Comm*, vol. 292, pp 702-708, 2002). Therefore, therapeutic agents that can inhibit β-secretase or BACE may be useful for the treatment of Alzheimer's disease.

The compounds of the present invention are useful for treating Alzheimer's disease by inhibiting the activity of β-secretase or BACE, thus preventing the formation of insoluble Aβ and arresting the production of Aβ.

SUMMARY OF THE INVENTION

The present invention is directed to tertiary carbinamine compounds having substituted heterocycles, which are useful as inhibitors of the β-secretase enzyme, and are useful in the treatment of diseases in which the β-secretase enzyme is involved, such as Alzheimer's disease. The invention is also directed to pharmaceutical compositions comprising these compounds, and the use of these compounds and compositions in the treatment of such diseases in which the β-secretase enzyme is involved.

DETAILED DESCRIPTION OF THE INVENTION

The present invention is directed to compounds of formula (I):

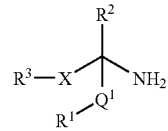

wherein:

X is a heteroaryl group having 5 or 6 ring atoms;

$Q^1$ is —$C_{0-3}$ alkylene, wherein said alkylene is unsubstituted or substituted with one or more
  (1) halo,
  (2) —$C_{3-12}$ cycloalkyl,
  (3) —OH,
  (4) —CN,
  (5) —O—$C_{1-10}$ alkyl, and
  (6) —$C_{1-10}$ alkyl;

$R^1$ is selected from the group consisting of
  (1) —$C_{6-10}$ aryl,
  (2) heteroaryl,
  (3) —$C_{10}$ alkyl, and
  (4) —$C_{3-8}$ cycloalkyl, said cycloalkyl optionally fused to a $C_{6-10}$ aryl group
wherein said $R^1$ alkyl, cycloalkyl, aryl or heteroaryl moiety is unsubstituted or substituted with one or more
  (a) halo,
  (b) —$C_{1-10}$ alkyl, wherein said alkyl is unsubstituted or substituted with halogen,
  (c) —OH,
  (d) —CN,
  (e) —O—$C_{1-10}$ alkyl,
  (f) —$C_{3-12}$ cycloalkyl, and
  (g) —$NR^aR^b$, wherein $R^a$ and $R^b$ are selected from the group consisting of
    (i) hydrogen,
    (ii) $C_{1-10}$ alkyl, and
    (iii) $C_{0-6}$ alkylene-$C_{6-10}$ aryl,
    or $R^a$ and $R^b$ are linked together with the N atom to form a carbocyclic group having four or five ring carbon atoms, wherein one or more of the ring carbon atoms may be replaced with an N, O or S atom, or a —(C=O)— or —$SO_2$— group;

$R^2$ is selected from the group consisting of
  (1) hydrogen,
  (2) —$C_{1-10}$ alkyl, and
  (3) —$C_{2-10}$ alkenyl, wherein said $R^2$ alkyl or alkenyl is unsubstituted or substituted with one or more
  (a) halo,
  (b) —$C_{3-12}$ cycloalkyl,
  (c) —OH,
  (d) —CN,
  (e) —O—$C_{1-10}$ alkyl,
  (f) —$C_{6-10}$ aryl, or
  (g) heteroaryl,
  and said alkyl, cycloalkyl, aryl or heteroaryl moiety above is unsubstituted or substituted with one or more
    (i) halo,
    (ii) —OH,
    (iii) —CN,
    (iv) —O—$C_{1-10}$ alkyl,
    (v) —$C_{1-10}$ alkyl, or
    (vi) —$C_{3-12}$ cycloalkyl;
$R^3$ is selected from the group consisting of
  (1) —$C_{0-3}$ alkylene-$C_{6-10}$ aryl,
  (2) —$C_{0-3}$ alkylene-heteroaryl,
  (3) —$C_{0-3}$ alkylene-N-carbocyclic group, said N-carbocyclic group having from 3 to 12 ring carbon atoms and optionally having one ring double bond, wherein one or more of the ring carbon atoms may be replaced with an N, O or S atom, or a —NH—, —(C=O)— or —$SO_2$— group, said N-carbocyclic group optionally fused to a $C_{6-10}$ aryl,
  (4) —$C_{0-3}$ alkylene-C-carbocyclic group, said C-carbocyclic group having from 3 to 12 ring carbon atoms and optionally having one ring double bond, wherein one or more of the ring carbon atoms may be replaced with an N, O or S atom, or a —NH—, —(C=O)— or —$SO_2$— group, said C-carbocyclic group optionally fused to a $C_{6-10}$ aryl,
  (5) —$C_{0-3}$ alkylene-$Q^4$-$C_{1-10}$ alkyl,
  (6) —$C_{0-3}$ alkylene-$Q^4$-$C_{2-10}$ alkenyl,
  (7) —$C_{0-3}$ alkylene-$Q^4$-$C_{2-10}$ alkynyl, or
  (8) —$C_{0-3}$ alkylene-$Q^4$-$C_{0-3}$ alkylene-$C_{6-10}$ aryl,
    wherein said $R^3$ alkyl, alkylene, alkenyl, alkynyl, N-carbocyclic, C-carbocyclic, aryl and heteroaryl moieties are unsubstituted or substituted with one or more
    (a) halo,
    (b) —OH,
    (c) —CN,
    (d) —$NO_2$,
    (e) —$C_{1-10}$ alkyl,
    (f) —O—$C_{1-10}$ alkyl,
    (g) —$C_{3-12}$ cycloalkyl,
    (h) —$C_{0-3}$ alkylene-$C_{6-10}$ aryl,
    (i) —$C_{0-3}$ alkylene-$C_{6-10}$ aryl,
    (j) —C(=O)—(O)$_m$—$C_{1-10}$ alkyl,
    (k) —C(=O)—(O)$_m$—$C_{0-3}$ alkylene—$C_{6-10}$ aryl,
    (l) —S(=O)$_2$—$C_{1-10}$ alkyl,
    (m) —S(=O)$_2$—$C_{0-3}$ alkylene-$C_{6-10}$ aryl,
    (n) heteroaryl,
    (o) —C(=O)—$C_{1-10}$ alkyl,
    (p) —$C_{0-3}$ alkylene-N-carbocyclic group, said N-carbocyclic group having from 3 to 12 ring carbon atoms and optionally having one ring double bond, wherein one or more of the ring carbon atoms may be replaced with an N, O or S atom, or a —NH—, —(C=O)— or —$SO_2$— group, said N-carbocyclic group optionally fused to a $C_{6-10}$ aryl,
    (q) —$CO_3$ alkylene-C-carbocyclic group, said C-carbocyclic group having from 3 to 12 ring carbon atoms and optionally having one ring double bond, wherein one or more of the ring carbon atoms may be replaced with an N, O or S atom, or a —NH—, —(C=O)— or —$SO_2$— group, said C-carbocyclic group optionally fused to a $C_{6-10}$ aryl,
    (r) —(C=O)—OH,
    (s) —$C_{0-3}$ alkylene-$(Q^2)_m$—NR$^c$R$^d$, wherein R$^c$ and R$^d$ are selected from the group consisting of
      (i) hydrogen,
      (ii) $C_{1-10}$ alkyl, and
      (iii) $C_{0-6}$ alkylene-$C_{6-10}$ aryl,
      or R$^c$ and R$^d$ are linked together with the N atom to form a carbocyclic group having four or five ring carbon atoms, wherein one or more of the ring carbon atoms may be replaced with an N, O or S atom, or a —(C=O)— or —$SO_2$— group,
    and said alkyl, alkylene, cycloalkyl, C-carbocyclic, N-carbocyclic, aryl or heteroaryl moiety above is unsubstituted or substituted with one or more
      (i) halo,
      (ii) —OH,
      (iii) —CN,
      (iv) —$C_{1-10}$ alkyl,
      (v) —$C_{2-10}$ alkenyl,
      (vi) —$C_{2-10}$ alkynyl,
      (vii) —O—$C_{1-10}$ alkyl,
      (viii) —$C_{3-12}$ cycloalkyl,
      (ix) —$C_{0-3}$ alkylene —$C_{6-10}$ aryl,
      (x) —C(=O)—(O)$_m$—$C_{1-10}$ alkyl, or
      (xi) —C(=O)—(O)$_m$—$C_{0-3}$ alkylene—$C_{6-10}$ aryl;
and $Q^2$, $Q^3$ and $Q^4$ are selected from the group consisting of
  (a) —S(=O)$_n$—,
  (b) —S—,
  (c) —O—,
  (d) —NR$^e$—
  (e) —NR$^e$—S(=O)$_n$—,
  (f) —NR$^e$—C(=O)—(O)$_m$—
  (g) —C(=O)—(O)$_m$—
  (h) —O—C(=O)—, and (i) 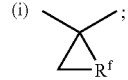

wherein R$^e$ is selected from the group consisting of
  (i) hydrogen,
  (ii) —$C_{1-10}$ alkyl,
  (iii) —$C_{0-3}$ alkylene-$C_{6-10}$ aryl,
  (iv) heteroaryl,
  (v) —$C_{0-3}$ alkylene-$Q^3$-$C_{1-10}$ alkyl,
  (vi) —$C_{0-3}$ alkylene-$Q^3$-$C_{2-10}$ alkenyl,
  (vii) —$C_{0-3}$ alkylene-$Q^3$-$C_{2-10}$ alkynyl, or
  (viii) —$C_{0-3}$ alkylene-$Q^3$-$C_{0-3}$ alkyl-$C_{6-10}$ aryl,
and R$^f$ is a one to four cyclic carbon chain, wherein one or more of the cyclic carbon atoms may be replaced with an N, O or S atom, or a —(C=O) or $SO_2$ group;
m is 0 or 1,
n is 1 or 2,
and pharmaceutically acceptable salts thereof, and individual enantiomers and diastereomers thereof.

The present invention is also directed to the use of the compounds disclosed herein as inhibitors of β-secretase enzyme activity or β-site amyloid precursor protein-cleaving enzyme ("BACE") activity, in a patient or subject such as a mammal in need of such inhibition, comprising the administration of an effective amount of the compound. The terms "β-secretase enzyme," "β-site amyloid precursor protein-cleaving enzyme," and "BACE" are used interchangeably in this specification. In addition to humans, a variety of other mammals can be treated according to the method of the present invention.

The present invention is further directed to a method for the manufacture of a medicament or a composition for inhibiting β-secretase enzyme activity in humans and animals comprising combining a compound of the present invention with a pharmaceutical carrier or diluent.

In preferred embodiments of the invention, X is a five or six membered heteroaryl selected from the group consisting of

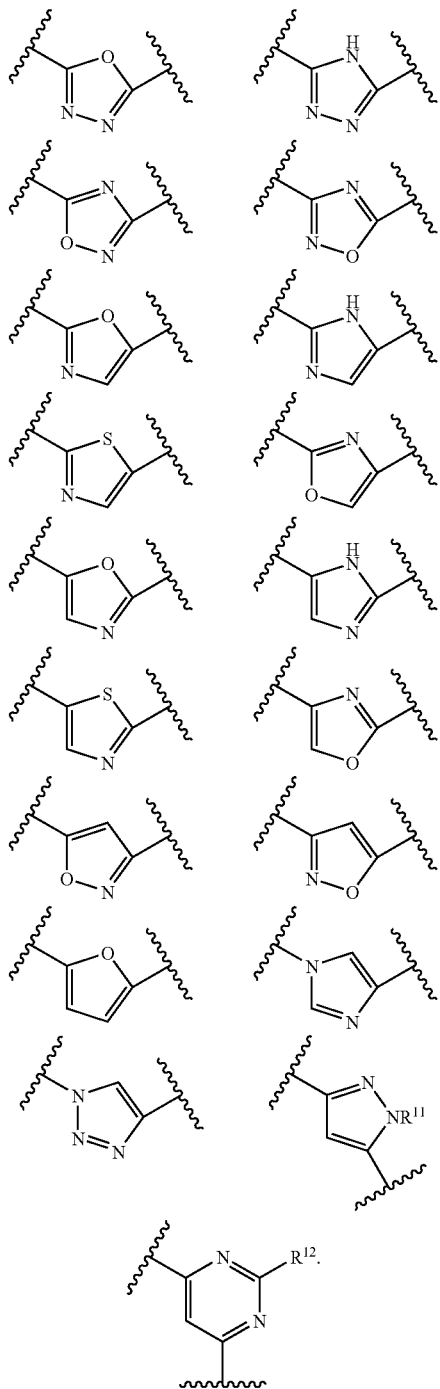

Particularly preferred X groups include:

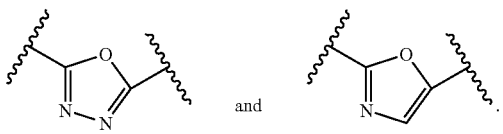

In preferred embodiments of the invention, $Q^1$ is $CH_2$. In more preferred embodiment of the invention, $Q^1$ is $CH_2$ and $R^1$ is phenyl (preferably unsubstituted phenyl).

In preferred embodiments of the invention, $R^2$ is $—C_{1-10}$ alkyl, more preferably $—C_{1-3}$ alkyl, most preferably unsubstituted $—C_{1-3}$ alkyl (preferably unsubstituted methyl).

In preferred embodiments, $R^3$ is selected from the group consisting of
(1) $—C_{0-3}$ alkylene-$C_{6-10}$ aryl,
(2) $—C_{0-3}$ alkylene-heteroaryl,
(3) $—C_{0-3}$ alkylene-N-carbocyclic group, and
(4) $—C_{0-3}$ alkylene-C-carbocyclic group, optionally substituted as above. Preferred heteroaryl groups include 6-membered heteroaryl rings having one nitrogen, such as pyridyl.

In other preferred embodiments, $R^3$ is selected from the group consisting of $—C_0$ alkylene-$C_{6-10}$ aryl and $C_0$ alkylene-heteroaryl. Preferred heteroaryl groups have five or six ring atoms.

Thus, in one embodiment, the compounds of the invention are compounds of formula (II)

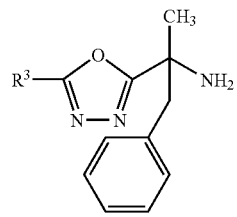

More preferably, the compounds of the invention are compounds of formula (II')

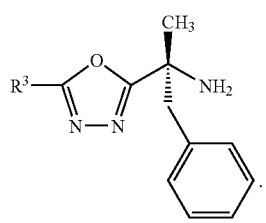

In certain embodiments of the compounds of formula (II) and (II'), $R^3$ is $—C_{0-3}$ alkylene-$C_{6-10}$ aryl or $—C_{0-3}$ alkylene-heteroaryl, wherein said heteroaryl has from 5 to 10 ring atoms, optionally substituted as defined above.

Another embodiment of the present invention includes a compound which is selected from the title compounds of the following Examples and pharmaceutically acceptable salts thereof.

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Preferred alkyl groups for use in the invention are $C_{1-6}$ alkyl groups, having from one to six carbon atoms. Exemplary alkyl groups include methyl, ethyl, n-propyl, isopropyl, n-butyl, isobutyl, tert-butyl, pentyl, hexyl, and the like.

As used herein, the term "alkylene," by itself or as part of another substituent, means a saturated straight or branched chain divalent hydrocarbon radical having the number of carbon atoms designated. The term $C_0$ alkylene (for example, in the radical "—$C_0$alkylene-$C_{6-10}$ aryl") represents a bond, and means that the alkylene group is absent.

As used herein, the term "alkenyl," by itself or as part of another substituent, means a straight or branched chain hydrocarbon radical having a single carbon-carbon double bond and the number of carbon atoms designated (e.g., $C_{2-10}$ alkenyl means an alkenyl group having from two to ten carbon atoms). Preferred alkenyl groups for use in the invention are $C_{2-6}$ alkenyl groups, having from two to six carbon atoms. Exemplary alkenyl groups include ethenyl and propenyl.

As used herein, the term "cycloalkyl," by itself or as part of another substituent, means a saturated monocyclic, polycyclic, spirocyclic or bridged cyclic hydrocarbon radical having the number of carbon atoms designated (e.g., $C_{3-12}$ cycloalkyl means a cycloalkyl group having from three to twelve carbon atoms). Preferred cycloalkyl groups include $C_{3-8}$ cycloalkyl groups, especially $C_{3-8}$ monocyclic cycloalkyl groups. Exemplary monocyclic cycloalkyl groups include cyclopropyl, cyclobutyl, cyclopentyl, cyclohexyl and the like. Exemplary bridged cycloalkyl groups include adamantly and norbornyl.

As used herein, the term "carbocyclic," by itself or as part of another substituent, means a cycloalkyl group as defined above, or a non-aromatic heterocyclic group. A non-aromatic heterocyclic group, by itself or as part of another substituent, means a carbocyclic group as defined above, optionally having a single ring double bond, in which one or more of the ring carbon atoms is replaced with a heteroatom (such as N, S or O), or a ring $SO_2$ or —(C═O)— group. For example, a non-aromatic heterocyclic ring may contain a —C(═O)—O— or —C(═O)—N— group. Carbocyclic groups contemplated for use in the invention include single ring structures, fused ring structures, bridged ring structures or spirocyclic structures. Suitable non-aromatic heterocyclic groups for use in the invention include piperidinyl, piperazinyl, morpholinyl, tetrahydrofuranyl, tetrahydrothienyl, pyrrolidinyl, pyrazolidinyl and imidazolildinyl.

Carbocyclic groups may be fused to $C_{6-10}$ aryl or heteroaryl rings having from 5 to 10 ring atoms.

A "C-carbocyclic group" as used herein represents a carbocyclic radical which is attached at a cyclic carbon. Preferred C-carbocyclic groups have five or six ring atoms.

An "N-carbocyclic group" as used herein represents a carbocyclic radical which is attached at a cyclic nitrogen. Preferred N-carbocyclic groups have five or six ring atoms.

When a non-aromatic heterocyclic group as defined herein is substituted, the substituent may be bonded to a ring carbon atom of the heterocyclic group, or to a ring heteroatom (i.e., a nitrogen, oxygen or sulfur), which has a valence which permits substitution. Preferably, the substituent is bonded to a ring carbon atom. Similarly, when a non-aromatic heterocyclic group is defined as a substituent herein, the point of attachment may be at a ring carbon atom of the heterocyclic group, or on a ring heteroatom (i.e., a nitrogen, oxygen or sulfur), which has a valence which permits attachment. Preferably, the attachment is at a ring carbon atom.

As used herein, the term "aryl," by itself or as part of another substituent, means an aromatic or cyclic radical having the number of carbon atoms designated (e.g., $C_{6-10}$ aryl means an aryl group having from six to ten carbons atoms). Preferred aryl groups for use in the invention include phenyl and naphthyl.

The term "halo" or "halogen" includes fluoro, chloro, bromo and iodo.

As used herein, the term "heteroaryl," by itself or as part of another substituent, means an aromatic cyclic group having at least one ring heteroatom (O, N or S). Heteroaryl groups contemplated for use in the invention may be fused single or fused ring structures. Exemplary heteroaryl groups for use in the invention include pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl, benzofuranyl, indynyl and benzoxazolyl. Preferred heteroaryl groups have from five to ten ring atoms. More preferred heteroaryl groups have five or six ring atoms.

Heteroaryl groups as defined herein may be fused to a non-aromatic carbocyclic ring.

When a heteroaryl group as defined herein is substituted, the substituent may be bonded to a ring carbon atom of the heteroaryl group, or on a ring heteroatom (i.e., a nitrogen, oxygen or sulfur), which has a valence which permits substitution. Preferably, the substituent is bonded to a ring carbon atom. Similarly, when a heteroaryl group is defined as a substituent herein, the point of attachment may be at a ring carbon atom of the heteroaryl group, or at a ring heteroatom (i.e., a nitrogen, oxygen or sulfur), which has a valence which permits attachment. Preferably, the attachment is at a ring carbon atom.

Some of the compounds of the instant invention have at least one asymmetric center. Additional asymmetric centers may be present depending upon the nature of the various substituents on the molecule. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of these compounds.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer of a compound may be obtained by stereoselective synthesis using optically pure starting materials or reagents of known configuration by methods well known in the art.

The compounds claimed in this invention can be prepared according to the following general procedures.

In Scheme 1, an amino acid derivative of type 1 is converted to the corresponding hydrazinyl amide 3 via a two step sequence. To access commercially unavailable amino acid derivatives, a two step alkylation of glycine Schiff base 4 can be utilized. Schiff base deprotection, Boc protection and ester hydrolysis provides an alternate route to compound 2. The alkylation of 4 for the synthesis of 5 may be performed in an enantioselective manner as described in the literature (see: K. Maruoka et al, *J. Am. Chem. Soc.* 2000, 122, 5228-5229 and M. North et al, *Tetrahedron Lett.* 2003, 44, 2045-2048).

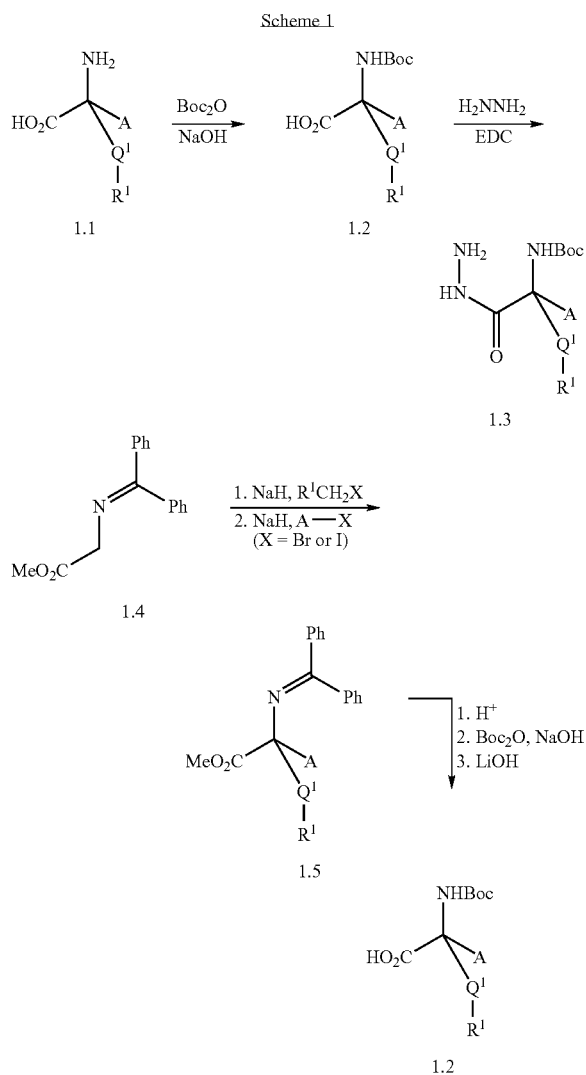

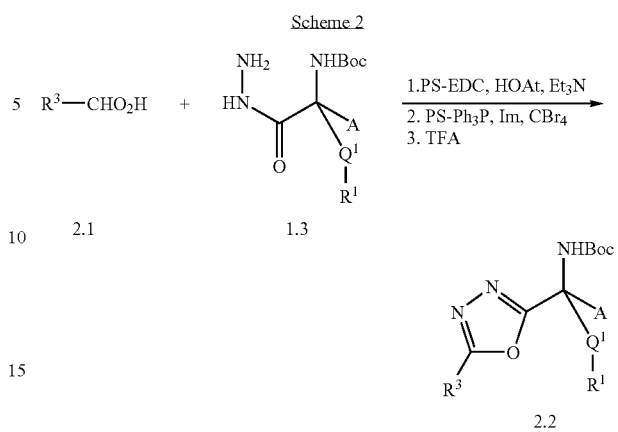

Scheme 2 depicts the synthesis of compounds of type 2.2. Amide bond formation is mediated by polymer supported (PS) EDC, which affords the coupled adduct upon quenching with macrophorous (MP) carbonate, filtration and concentration. Dehydration is accomplished using PS-Ph$_3$P, Im and CBr$_4$, where simple filtration and concentration provides the desired oxadiazole, which can then undergo Boc deprotection under acidic conditions.

The term "substantially pure" means that the isolated material is at least 90% pure, and preferably 95% pure, and even more preferably 99% pure as assayed by analytical techniques known in the art.

The term "pharmaceutically acceptable salts" refers to salts prepared from pharmaceutically acceptable non-toxic bases or acids including inorganic or organic bases and inorganic or organic acids. The compounds of the invention may be mono, di or tris salts, depending on the number of acid functionalities present in the free base form of the compound. Free bases and salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, trifluoroacetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, trifluoroacetic, maleic, phosphoric, sulfuric, fumaric, and tartaric acids.

The compounds of the present invention have utility in treating, ameliorating, controlling or reducing the risk of Alzheimer's disease. For example, the compounds may be useful for the prevention of dementia of the Alzheimer's type, as well as for the treatment of early stage, intermediate stage or late stage dementia of the Alzheimer's type. The compounds may also be useful in treating, ameliorating, controlling or reducing the risk of diseases mediated by abnormal cleavage of amyloid precursor protein (also referred to as APP), and other conditions that may be treated or prevented by inhibition of β-secretase. Such conditions include mild cognitive impairment, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jalcob disease, prion disorders, amyotrophic lateral sclerosis, progressive supranuclear palsy, head trauma, stroke, Down syndrome, pancreatitis, inclusion body myositis, other peripheral amyloidoses, diabetes and atherosclerosis.

The subject or patient to whom the compounds of the present invention is administered is generally a human being, male or female, in whom inhibition of β-secretase enzyme activity is desired, but may also encompass other mammals, such as dogs, cats, mice, rats, cattle, horses, sheep, rabbits, monkeys, chimpanzees or other apes or primates, for which inhibition of β-secretase enzyme activity or treatment of the above noted disorders is desired.

The compounds of the present invention may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of combinations of the compounds of the present invention with other drugs in either unit dose or kit form include combinations with anti-Alzheimer's agents, for example other beta-secretase inhibitors or gamma-secretase inhibitors; tau phosphorylation inhibitors; M1 receptor positive allosteric modulators; blockers of Aβ oligomer formation; 5-HT modulators, such as PRX-03140, GSK 742467, SGS-518, FK-962, SL-65.0155, SRA-333 and xaliproden; p25/CDK5 inhibitors; NK1/NK3 receptor antagonists; COX-2 inhibitors; HMG-CoA reductase inhibitors; NSAIDs including ibuprofen; vitamin E; anti-amyloid antibodies, including anti-amyloid humanized monoclonal antibodies; anti-inflammatory compounds such as (R)-flurbiprofen, nitroflurbiprofen, rosiglitazone, ND-1251, VP-025, HT-0712 and EHT-202; CB-1 receptor antagonists or CB-1 receptor inverse agonists; antibiotics such as doxycycline and rifampin; N-methyl-D-aspartate (NMDA) receptor antagonists, such as memantine and neramexane; cholinesterase inhibitors such as galantamine, rivastigmine, donepezil, tacrine, phenserine, ladostigil and ABT-089; growth hormone secretagogues such as ibutamoren, ibutamoren mesylate, and capromorelin; histamine $H_3$ antagonists such as ABT-834, ABT 829 and GSK 189254; AMPA agonists or AMPA modulators, such as CX-717, LY 451395 and S-18986; PDE IV inhibitors; $GABA_A$ inverse agonists; neuronal nicotinic agonists; selective M1 agonists; microtobubule affinity regulating kinase (MARK) ligands; P-450 inhibitors, such as ritonavir; or other drugs that affect receptors or enzymes that either increase the efficacy, safety, convenience, or reduce unwanted side effects or toxicity of the compounds of the present invention. The foregoing list of combinations is illustrative only and not intended to be limiting in any way.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by admixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the active ingredient in a vegetable oil, for example arachis oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, which may be formulated according to the known art, or may be administered in the form of suppositories for rectal administration of the drug.

The compounds of the present invention may also be administered by inhalation, by way of inhalation devices known to those skilled in the art, or by a transdermal patch.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician.

As used herein, the term "treatment" or "treating" means any administration of a compound of the present invention and includes (1) inhibiting the disease in an animal that is experiencing or displaying the pathology or symptomatology of the diseased (i.e., arresting further development of the pathology and/or symptomatology), or (2) ameliorating the disease in an animal that is experiencing or displaying the pathology or symptomatology of the diseased (i.e., reversing the pathology and/or symptomatology). The term "controlling" includes preventing treating, eradicating, ameliorating or otherwise reducing the severity of the condition being controlled.

The compositions containing compounds of the present invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage forms.

The compositions containing compounds of the present invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

When treating, ameliorating, controlling or reducing the risk of Alzheimer's disease or other diseases for which compounds of the present invention are indicated, generally satisfactory results are obtained when the compounds of the present invention are administered at a daily dosage of from about 0.1 mg to about 100 mg per kg of animal body weight, preferably given as a single daily dose or in divided doses two to six times a day, or in sustained release form. The total daily dosage is from about 1.0 mg to about 2000 mg, preferably from about 0.1 mg to about 20 mg per kg of body weight. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

Specific dosages of the compounds of the present invention, or pharmaceutically acceptable salts thereof, for administration include 1 mg, 5 mg, 10 mg, 30 mg, 80 mg, 100 mg, 150 mg, 300 mg and 500 mg. Pharmaceutical compositions of the present invention may be provided in a formulation comprising about 0.5 mg to 1000 mg active ingredient; more preferably comprising about 0.5 mg to 500 mg active ingredient; or 0.5 mg to 250 mg active ingredient; or 1 mg to 100 mg active ingredient. Specific pharmaceutical compositions useful for treatment may comprise about 1 mg, 5 mg, 10 mg, 30 mg, 80 mg, 100 mg, 150 mg, 300 mg and 500 mg of active ingredient.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The utility of the compounds in accordance with the present invention as inhibitors of β-secretase enzyme activity may be demonstrated by methodology known in the art. Enzyme inhibition is determined as follows.

ECL Assay: A homogeneous end point electrochemiluminescence (ECL) assay is employed using a biotinylated BACE substrate. The Km of the substrate is greater than 100 μM and can not be determined due to the limit of solubility of the substrate. A typical reaction contains approximately 0.1 nM enzyme, 0.25 μM of the substrate, and buffer (50 mM NaOAc, pH 4.5, 0.1 mg/ml BSA, 0.2% CHAPS, 15 mM EDTA and 1 mM deferoxamine) in a total reaction volume of 100 μl. The reaction proceeds for 30 min and is then stopped by the addition of 25 μL of 1 M Tris-HCl, pH 8.0. The resulting enzymatic product is assayed by adding a ruthenylated antibody which specifically recognizes the C-terminal residue of the product. Streptavidin coated magnetic beads are added into the solution and the samples are subjected to M-384 (Igen Inc., Gaithersburg, Md.) analysis. Under these conditions, less than 10% of substrate is processed by BACE 1. The enzyme used in these studies is soluble (transmembrane domain and cytoplasmic extension excluded) human protein produced in a baculovirus expression system. To measure the inhibitory potency for compounds, solutions of inhibitor in DMSO (12 concentrations of the inhibitors are prepared starting from 100 μM with three fold series dilution) are included in the reaction mixture (final DMSO concentration is 10%). All experiments are conducted at rt using the standard reaction conditions described above. To determine the $IC_{50}$ of the compound, a four parameter equation is used for curve fitting. The errors in reproducing the dissociation constants are typically less than two-fold.

HPLC assay: A homogeneous end point HPLC assay is employed with the substrate (coumarin-CO-REVNFE-VEFR), which is cleaved by BACE 1 to release the N-terminal fragment attached with coumarin. The Km of the substrate is greater than 100 μM and can not be determined due to the limit of solubility of the substrate. A typical reaction contains approximately 2 nM enzyme, 1.0 μM of the substrate, and buffer (50 mM NaOAc, pH 4.5, 0.1 mg/ml BSA, 0.2% CHAPS, 15 mM EDTA and 1 mM deferoxamine) in a total reaction volume of 100 μl. The reaction is proceeded for 30 min and the reaction is stopped by the addition of 25 μL of 1 M Tris-HCl, pH 8.0. The resulting reaction mixture is loaded on the HPLC and the product is separated from substrate with 5 min linear gradient. Under these conditions, less than 10% of substrate is processed by BACE 1. The enzyme used in these studies is soluble (transmembrane domain and cytoplasmic extension excluded) human protein produced in a baculovirus expression system. To measure the inhibitory potency for compounds, solutions of inhibitor in DMSO (12 concentrations of the inhibitors are prepared and the concentration rage is dependent on the potency predicted by ECL) are included in the reaction mixture (final DMSO concentration is 10%). All experiments are conducted at rt using the standard reaction conditions described above. To determine the $IC_{50}$ of the compound, four parameters equation is used for curve fitting. The errors in reproducing the dissociation constants are typically less than two-fold.

In particular, the compounds of the following examples had activity in inhibiting the beta-secretase enzyme in one or both of the aforementioned assays, generally with an $IC_{50}$ from about 1 nM to 500 μM. Such a result is indicative of the intrinsic activity of the compounds in use as inhibitors of beta-secretase enzyme activity.

Several methods for preparing the compounds of this invention are illustrated in the Schemes and Examples herein. Starting materials are made according to procedures known in the art or as illustrated herein. The following examples are provided so that the invention might be more fully understood. These examples are illustrative only and should not be construed as limiting the invention in any way.

Intermediate 1.2: (R)—N-(tert-butoxycarbonyl)-α-methylphenylalanine

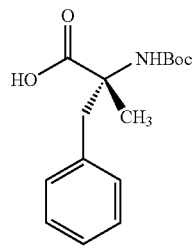

To a slurry of (R)-α-methyl phenylalanine (1.00 g, 5.58 mmol) in 20 μL dioxane was added 3N NaOH (7.4 μL, 22.32 mmol) and Boc$_2$O (1.28 g, 5.86 mmol). The reaction was allowed to proceed for 14 h. The pH was lowered to ~1 by adding 1N HCl dropwise, diluted with water, and the aqueous layer was extracted with EtOAc (3×). Dried combined organics over Na$_2$SO$_4$, filtered and concentrated to obtain the desired product as a white foam. This was used without further purification. $^1$H NMR (d$_4$-MeOH, 400 Mhz) δ 7.25-7.17 (m, 3H), 7.12 (d, J=6.6 Hz, 2H), 3.27 (d, J=13.4 Hz, 1H), 3.15 (d, J=13.4 Hz, 1H), 1.45 (s, 9H), 1.39 (s, 3H). LCMS [(M-Boc)+H]$^+$=180

Intermediate 1.3: (R)—N-(tert-butoxycarbonyl)-α-methylphenylalaninehydrazide

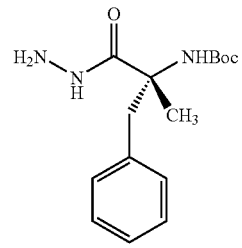

To a solution of (R)—N-Boc-α-methyl phenylalanine (1.50 g, 5.37 mmol) in 25 mL CH$_3$CN was added EDC (1.75 g, 9.13 mmol), followed by hydrazine (0.421 mL, 13.43 mmol). A white precipitate formed immediately, and the solution gradually turned clear over 1 h. The reaction was allowed to proceed at room temperature overnight, when it was quenched by the addition of saturated aqueous NaHCO$_3$ solution, and diluted with EtOAc. The layers were separated, and the aqueous layer was washed with fresh EtOAc (3×). The combined organic layers were dried over Na$_2$SO$_4$, filtered and concentrated to afford a white foam, which was used without further purification. $^1$H NMR (d$_4$-MeOH, 400 MHz) δ 7.27-7.20 (m, 3H), 7.11 (d, J=7.7 Hz, 2H), 3.30 (d, J=13.5 Hz, 1H), 3.02 (d, J=13.5 Hz, 1H), 1.46 (s, 9H), 1.31 (s, 3H). LCMS [[(M-Boc)+H]$^+$=194.

Example 1

(R)-2-[5-(5-methyl-1,3-diphenyl-1H-pyrazol-4-yl)-1,3,4-oxadiazol-2-yl]-1-phenylpropan-2-amine

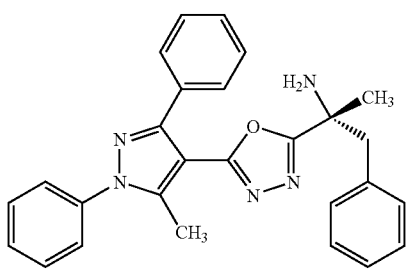

Step A: Amide Coupling

To a solution of 5-methyl-1,3-diphenyl-1H-pyrazole-4-carboxylic acid (0.051 g, 0.184 mmol, 1.8 equiv) and Intermediate 1.3 (0.030 g, 0.102 mmol, 1.0 equiv) in 3 mL CH$_2$Cl$_2$ was added HOAt (0.007 g, 0.50 mmol, 0.50 equiv.), diisopropylethylamine (0.034 mL, 0.200 mmol, 2 equiv.) and polymer supported DCC (0.143 g, 0.200 mmol, 2 equiv. at 1.4 mmol/g loading on resin). After 16 h of agitation, the reaction was quenched by the addition of macroporous carbonate (0.190 g, 0.540 mmol, 5.4 equiv, at 5.4 mmol/g resin loading). The reaction was filtered and concentrated. LC/MS [M+H]$^+$=554.

Step B: Dehydration

To a solution of adduct from Step A in 3 mL CH$_2$Cl$_2$ was added imidazole (0.035 g, 0.515 mmol, 5 equiv.), CBr$_4$ (0.171 g, 0.515 mmol, 5 equiv.) and polymer supported Ph$_3$P (0.230 g, 0.515 mmol, 5 equiv at 2.21 mmol/g resin loading). The reaction was agitated for 1.5 h, filtered and concentrated. The residue was dissolved in DMF and purified by preparative HPLC (5->95% CH$_3$CN/H$_2$O, 0.1% added TFA, C18 PRO YMC 20×150 mm) to afford the desired oxadiazole as a viscous oil. LC/MS [M+H]$^+$=536.

Step C: Boc Deprotection

To a solution of adduct from Step B in 2 mL CH$_2$Cl$_2$ was added TFA (0.200 mL, 2.05 mmol, 20.0 equiv.). After 16 h, the reaction was concentrated, redissolved in DMF and purified by preparative HPLC (5->95% CH$_3$CN/H$_2$O, 0.1% added TFA, C18 PRO YMC 20×150 mm), and the product containing fractions were freeze dried to afford (R)-2-[5-(5-methyl-1,3-diphenyl-1H-pyrazol-4-yl)-1,3,4-oxadiazol-2-yl]-1-phenylpropan-2-amine as a white solid. $^1$H NMR (400 MHz, d$_4$-MeOH) d 7.61-7.55 (m, 5H), 7.49-7.46 (m, 2H), 7.39-7.30 (m, 3H), 7.29-7.27 (m, 3H), 6.92 (dd, J=7.1, 1.5 Hz, 2H), 3.27 (d, J=13.5 Hz, 1H), 3.19 (d, J=13.5 Hz, 1H), 2.59 (s, 3H), 1.60 (s, 3H). Exact mass calculated for C$_{27}$H$_{26}$N$_5$O [(M+H)$^+$]=436.2132; measured=436.2100.

The following additional compounds were made according to the general scheme described above, using starting materials and reagents described above, or by using materials and reagents which are commercially available or may be obtained by the application of standard techniques of organic synthesis to commercially available reagents. Mass spectrometry data is provided below.

| Example No. | Structure | MS: M + 1 |
|---|---|---|
| 2 | 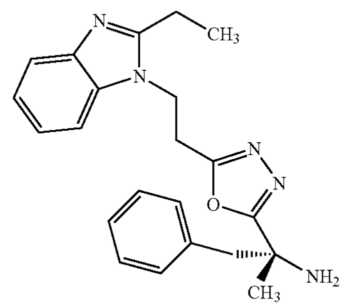 | 376 |
| 3 | 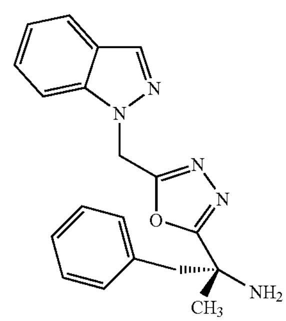 | 334 |
| 4 | 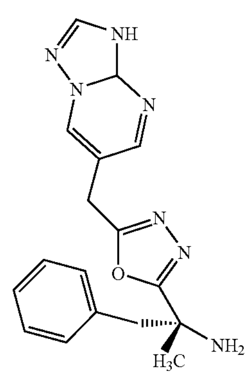 | 334 |

-continued
| Example No. | Structure | MS: M + 1 |
|---|---|---|
| 5 | 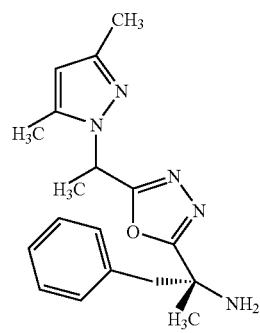 | 326 |
| 6 | 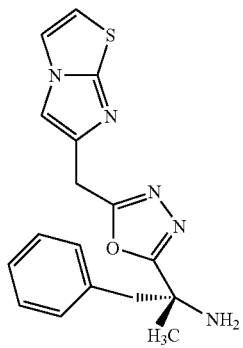 | 340 |
| 7 | 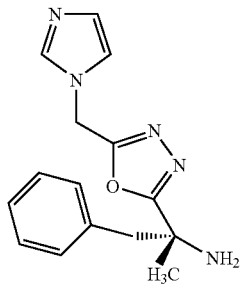 | 284 |
| 8 | 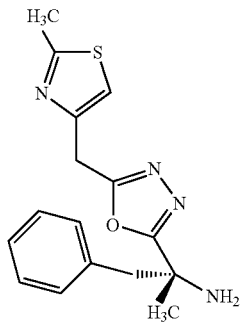 | 315 |

-continued
| Example No. | Structure | MS: M + 1 |
|---|---|---|
| 9 | 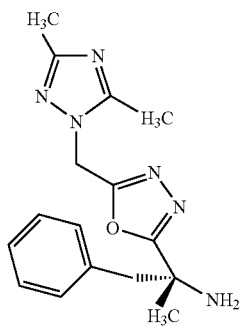 | 313 |
| 10 | 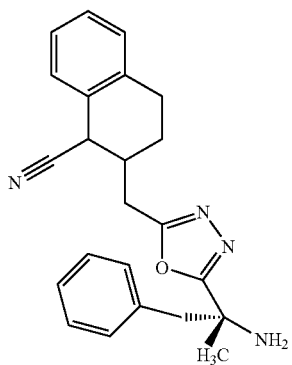 | 373 |
| 11 | 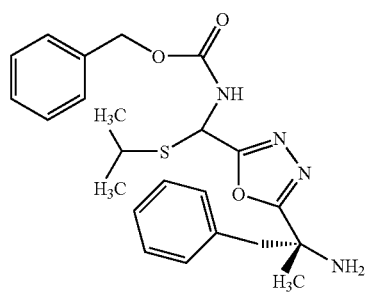 | 441 |
| 12 | 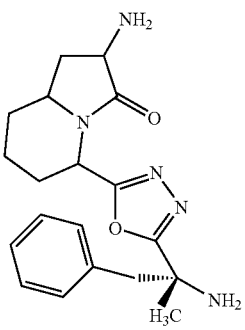 | 356 |

| Example No. | Structure | MS: M + 1 |
|---|---|---|
| 13 | 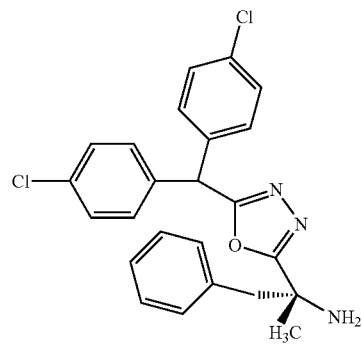 | 438 |
| 14 | 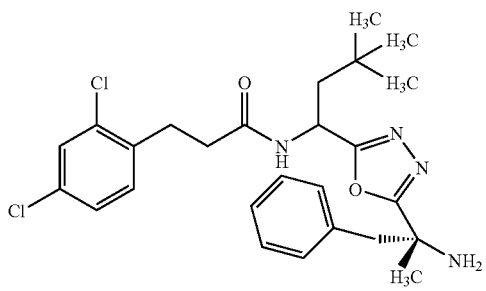 | 503 |
| 15 | 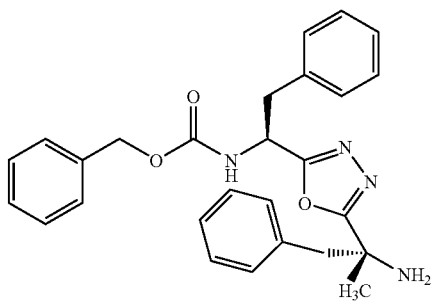 | 457 |
| 16 | 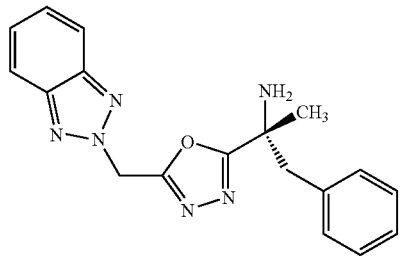 | 335 |
| 17 | 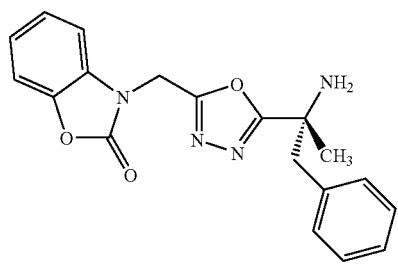 | 351 |

-continued
| Example No. | Structure | MS: M + 1 |
|---|---|---|
| 18 | 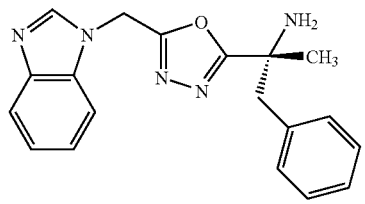 | 334 |
| 19 | 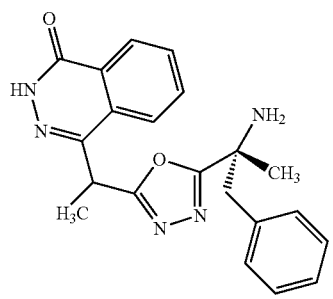 | 376 |
| 20 | 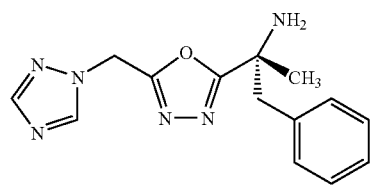 | 285 |
| 21 | 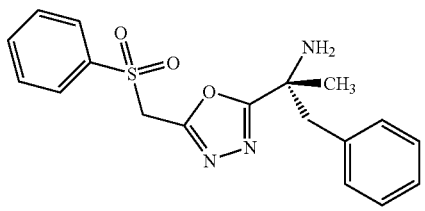 | 356 |
| 22 | 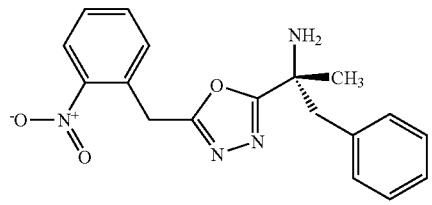 | 339 |
| 23 | 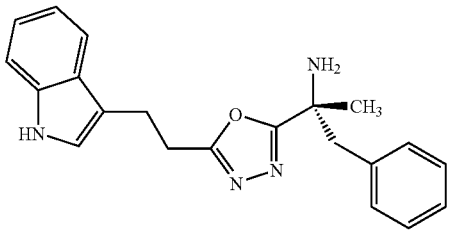 | 347 |

-continued
| Example No. | Structure | MS: M + 1 |
|---|---|---|
| 24 | 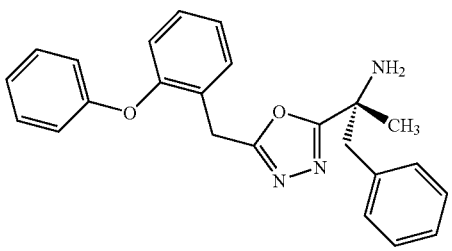 | 386 |
| 25 | 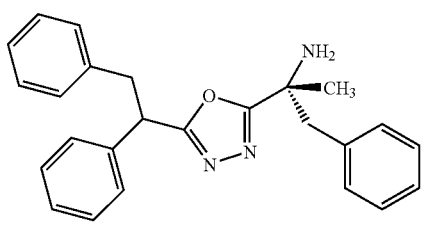 | 384 |
| 26 | 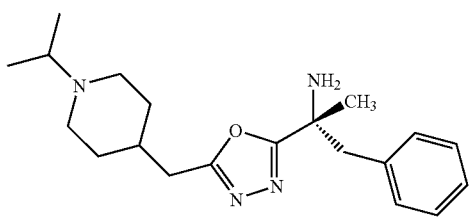 | 343 |
| 27 | 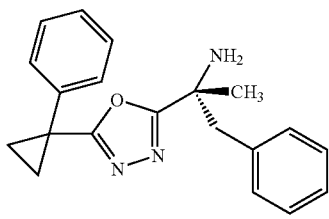 | 320 |
| 28 | 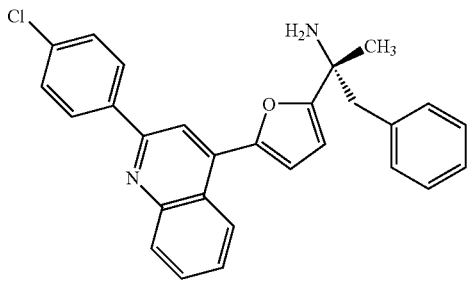 | 439 |
| 29 | 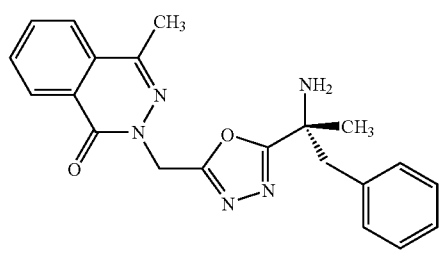 | 376 |

-continued
| Example No. | Structure | MS: M + 1 |
|---|---|---|
| 30 | 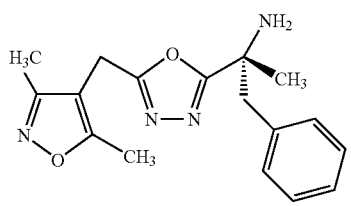 | 313 |
| 31 | 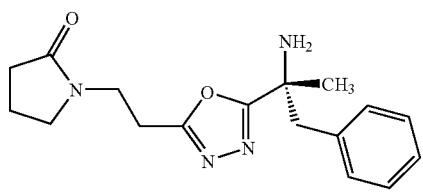 | 315 |
| 32 | 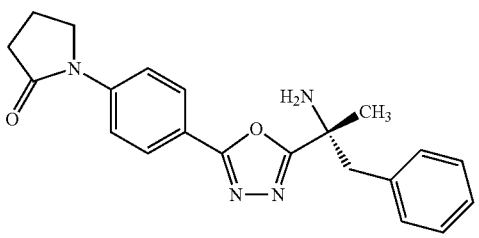 | 363 |
| 33 | 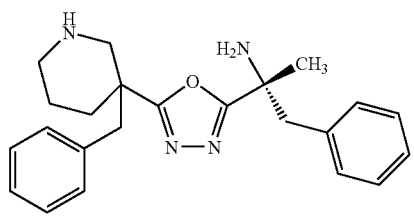 | 377 |
| 34 | 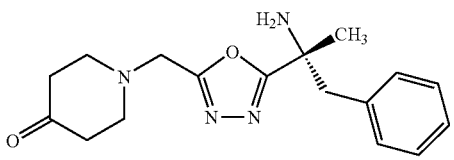 | 315 |
| 35 | 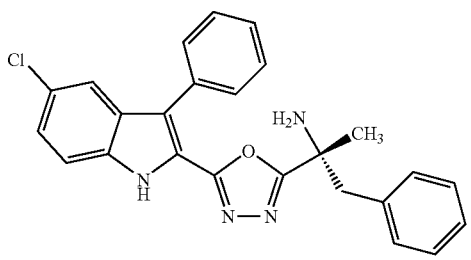 | 429 |

-continued

| Example No. | Structure | MS: M + 1 |
|---|---|---|
| 36 | 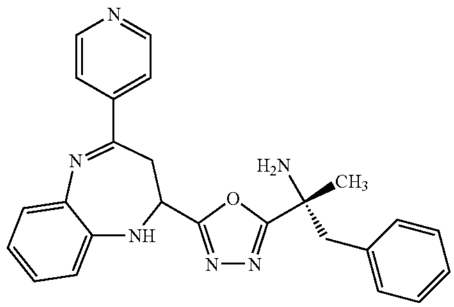 | 425 |
| 37 | 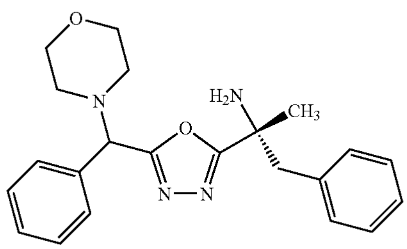 | 395 |
| 38 | 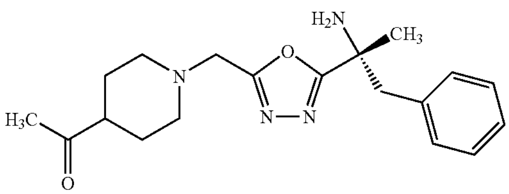 | 343 |
| 39 | 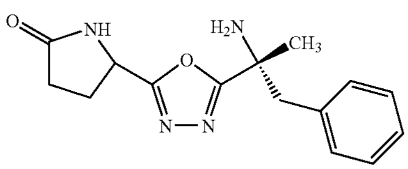 | 287 |
| 40 | 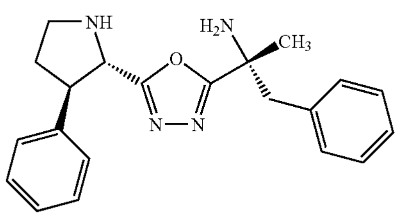 | 349 |
| 41 | 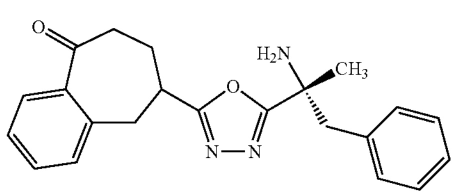 | 362 |
| 42 | 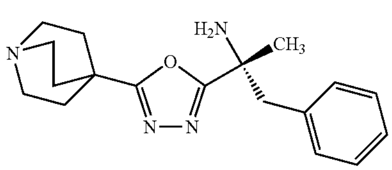 | 313 |

-continued
| Example No. | Structure | MS: M + 1 |
|---|---|---|
| 43 | 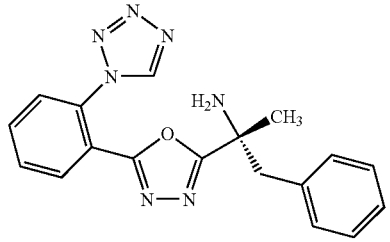 | 348 |
| 44 | 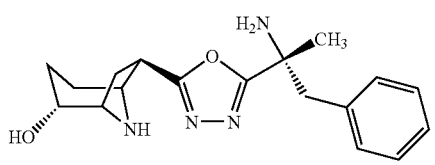 | 329 |
| 45 | 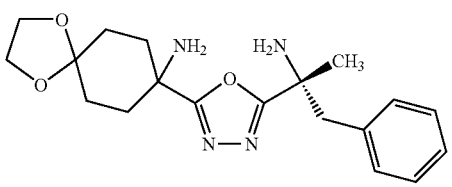 | 359 |
| 46 | 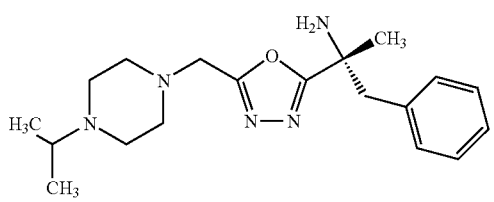 | 360 |
| 47 | 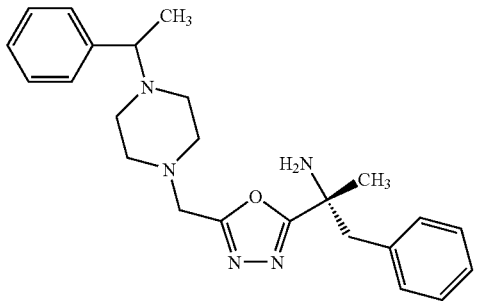 | 406 |
| 48 | 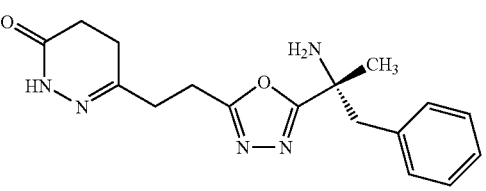 | 328 |
| 49 | 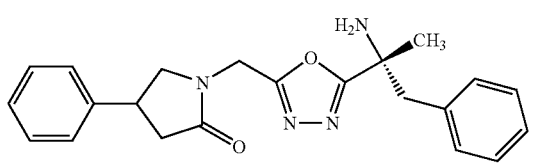 | 377 |

| Example No. | Structure | MS: M + 1 |
|---|---|---|
| 50 | 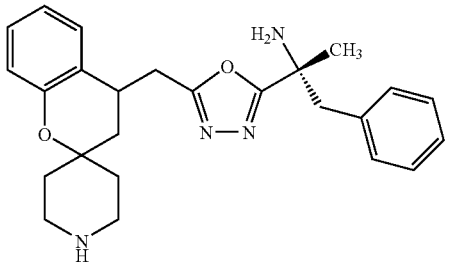 | 419 |
| 51 | 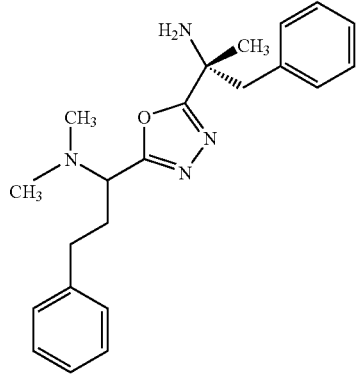 | 365 |
| 52 | 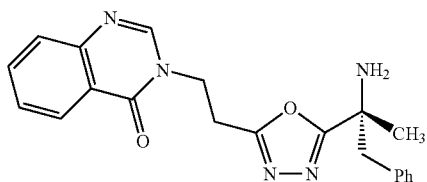 | 376 |
| 53 | 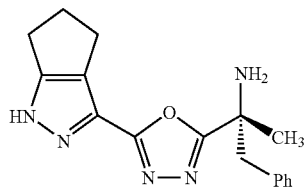 | 310 |
| 54 | 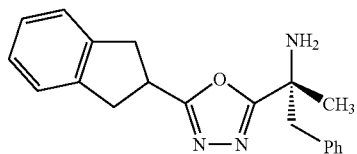 | 320 |
| 55 | 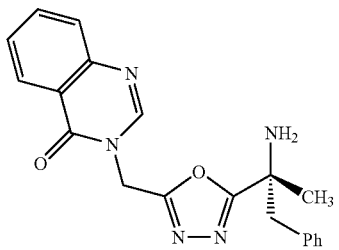 | 362 |

-continued
| Example No. | Structure | MS: M + 1 |
|---|---|---|
| 56 | 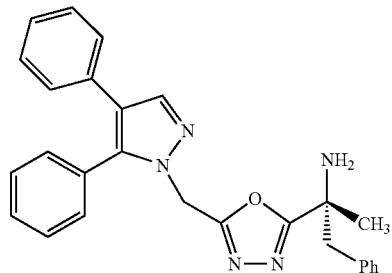 | 436 |
| 57 | 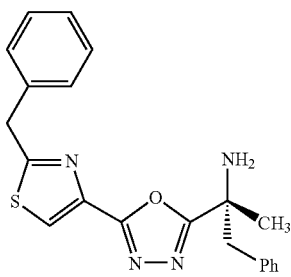 | 377 |
| 58 | 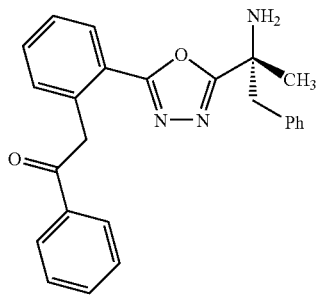 | 398 |
| 59 | 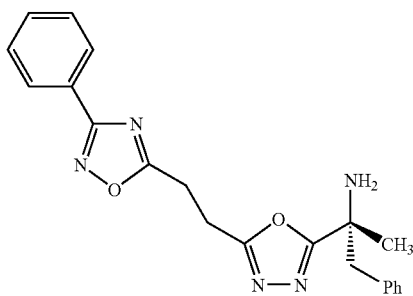 | 376 |
| 60 | 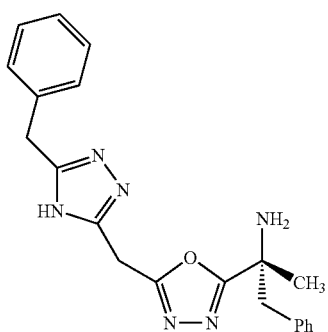 | 375 |

| Example No. | Structure | MS: M + 1 |
|---|---|---|
| 61 | 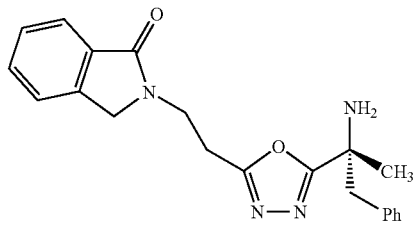 | 363 |
| 62 | 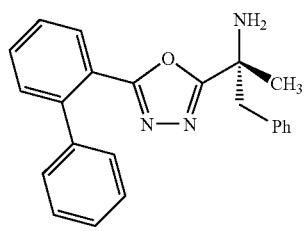 | 356 |
| 63 | 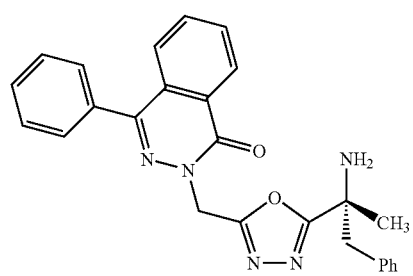 | 438 |
| 64 | 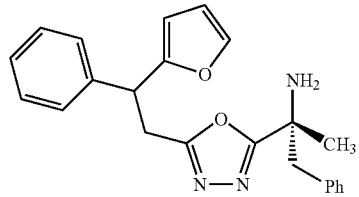 | 374 |
| 65 | 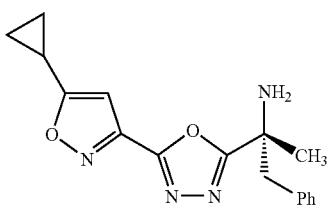 | 311 |
| 66 | 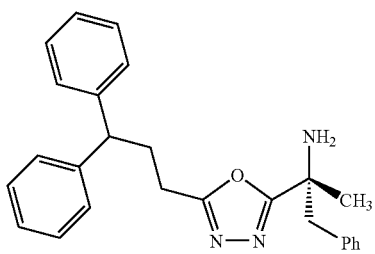 | 398 |

| Example No. | Structure | MS: M + 1 |
|---|---|---|
| 67 | 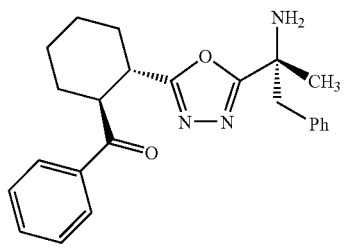 | 390 |
| 68 | 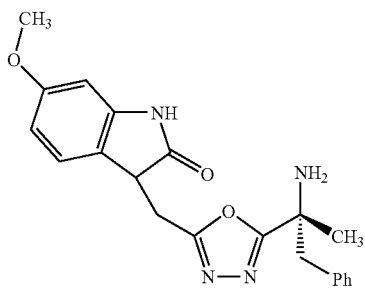 | 379 |
| 69 | 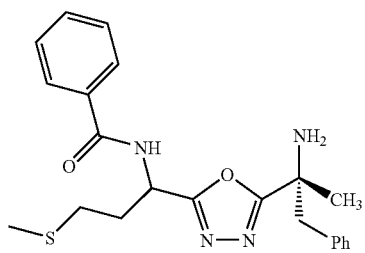 | 411 |
| 70 | 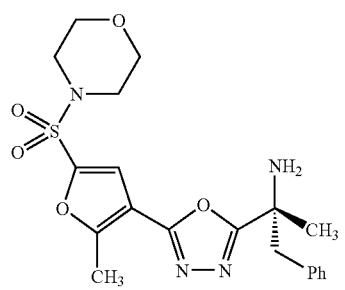 | 433 |
| 71 | 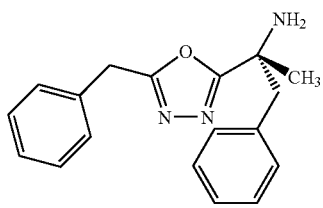 | 294 |
| 72 | 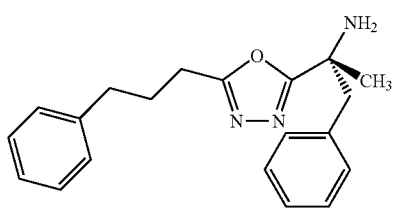 | 322 |

-continued
| Example No. | Structure | MS: M + 1 |
|---|---|---|
| 73 | 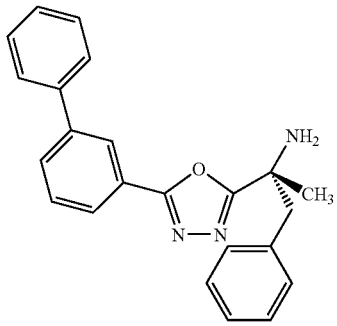 | 356 |
| 74 | 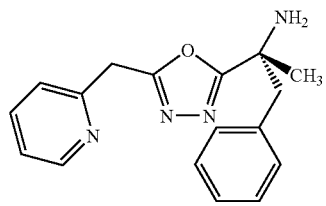 | 295 |
| 75 | 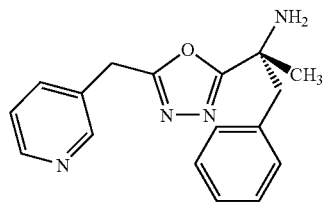 | 295 |
| 76 | 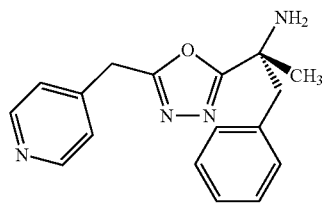 | 295 |
| 77 | 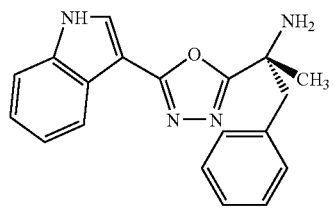 | 319 |
| 78 | 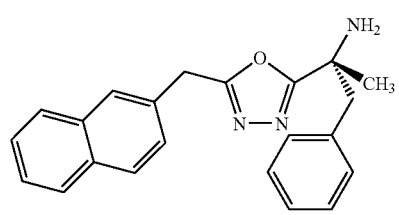 | 344 |

-continued
| Example No. | Structure | MS: M + 1 |
|---|---|---|
| 79 | 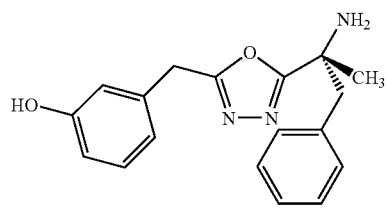 | 310 |
| 80 | 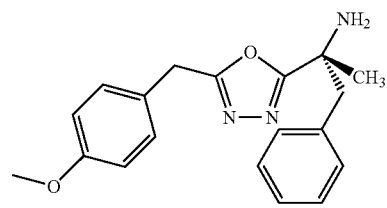 | 324 |
| 81 | 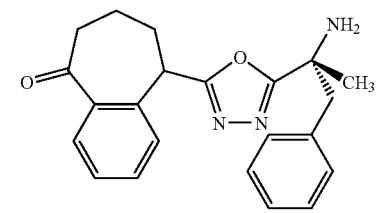 | 362 |
| 82 | 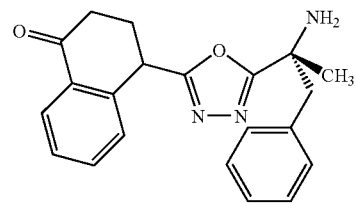 | 348 |
| 83 | 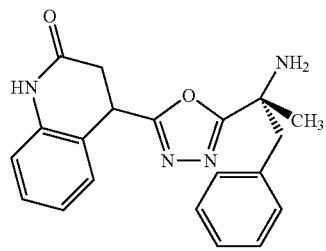 | 349 |
| 84 | 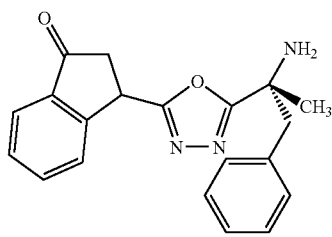 | 334 |

-continued

| Example No. | Structure | MS: M + 1 |
|---|---|---|
| 85 | 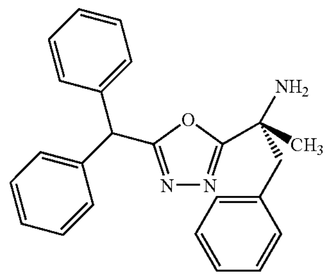 | 370 |
| 86 | 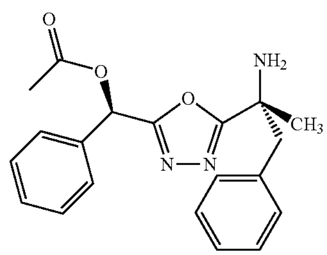 | 352 |
| 87 | 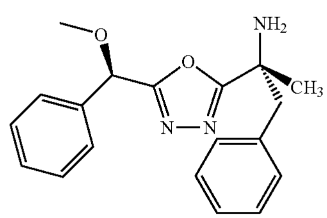 | 324 |
| 88 | 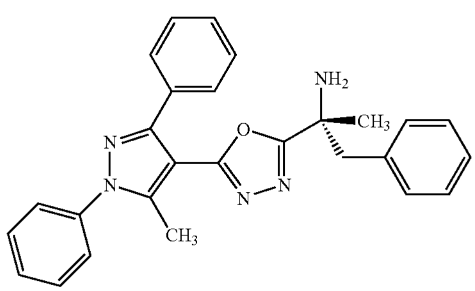 | 436 |
| 89 | 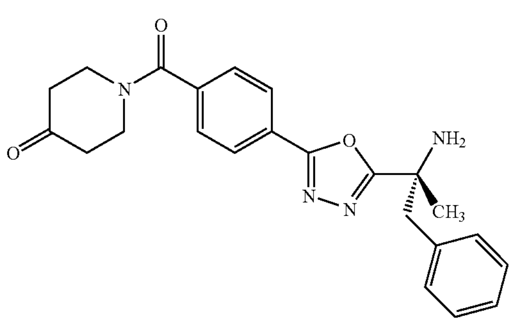 | 405 |

| Example No. | Structure | MS: M + 1 |
|---|---|---|
| 90 | 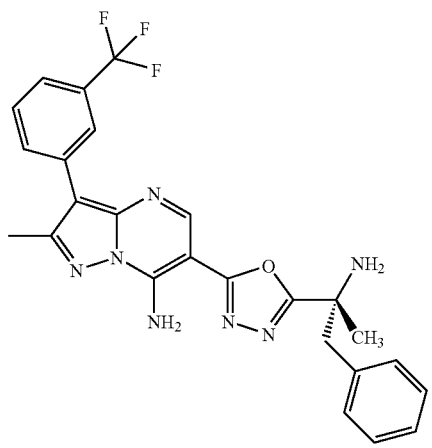 | 494 |
| 91 | 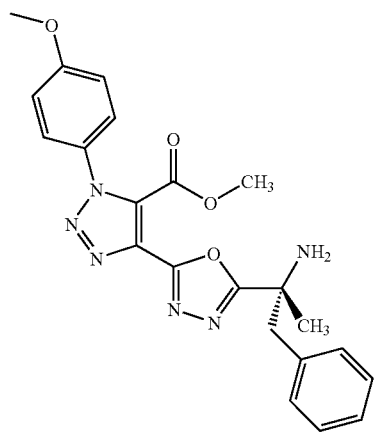 | 435 |
| 92 | 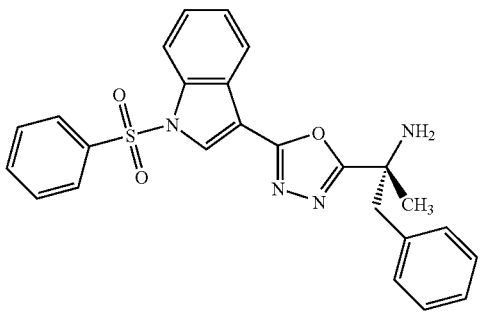 | 459 |
| 93 | 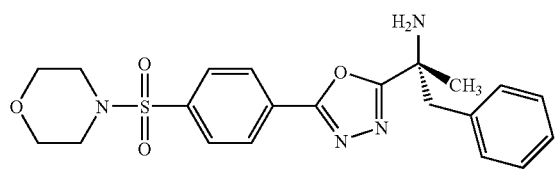 | 429 |

| Example No. | Structure | MS: M + 1 |
|---|---|---|
| 94 | 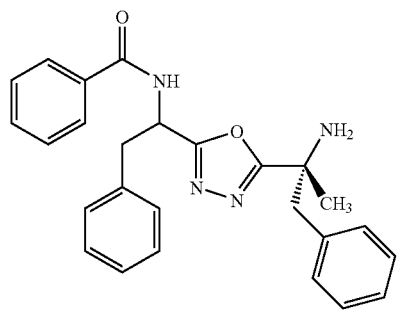 | 427 |
| 95 | 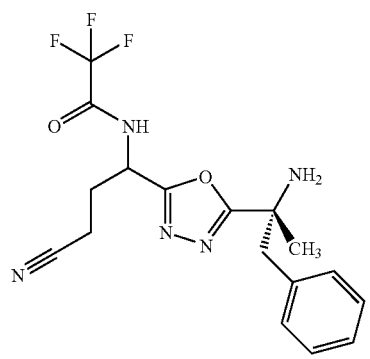 | 382 |
| 96 | 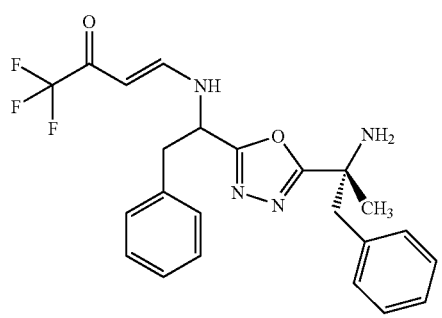 | 445 |
| 97 | 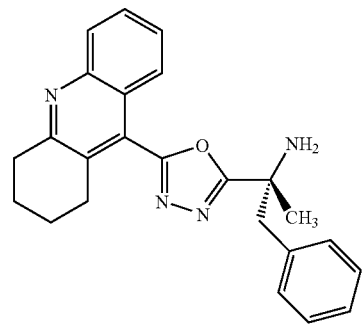 | 385 |

| Example No. | Structure | MS: M + 1 |
| --- | --- | --- |
| 98 | 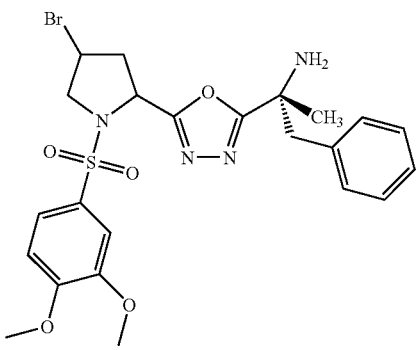 | 551 |
| 99 | 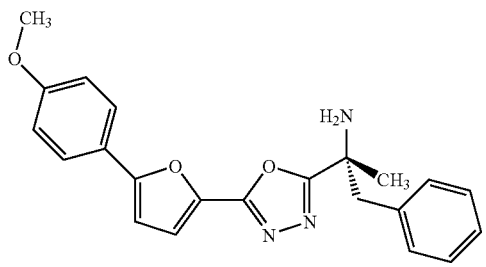 | 376 |
| 100 | 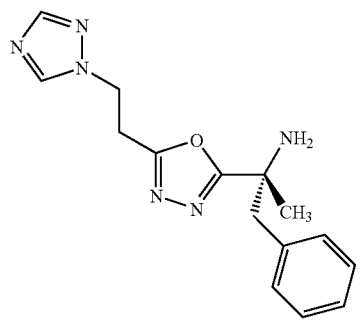 | 299 |
| 101 | 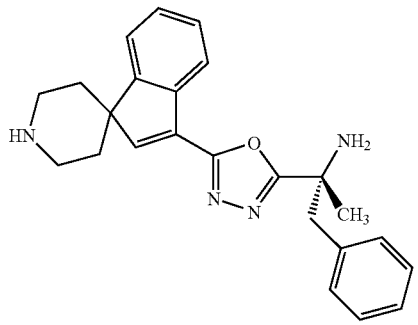 | 387 |
| 102 | 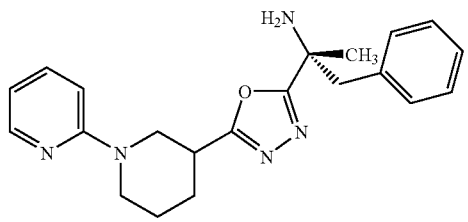 | 364 |

-continued
| Example No. | Structure | MS: M + 1 |
|---|---|---|
| 103 | 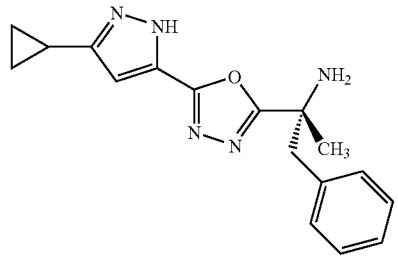 | 310 |
| 104 | 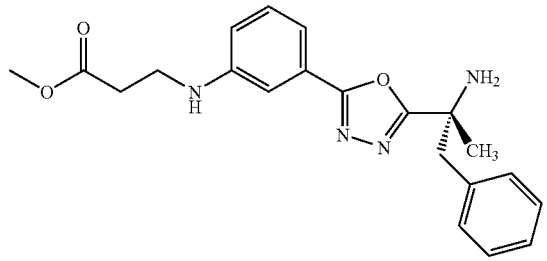 | 381 |
| 105 | 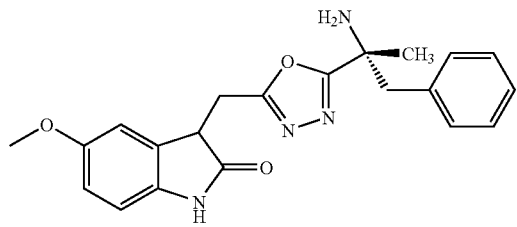 | 379 |
| 106 | 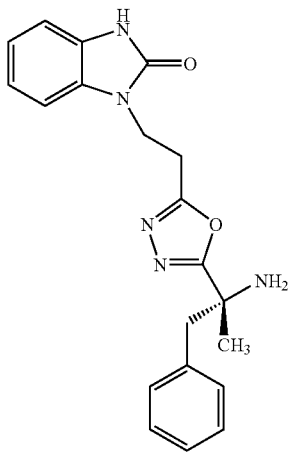 | 364 |
| 107 | 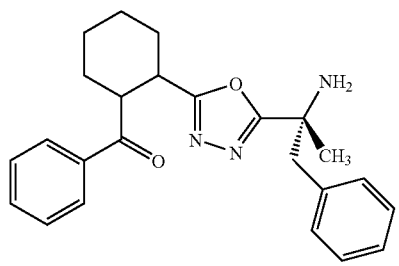 | 390 |

-continued

| Example No. | Structure | MS: M + 1 |
|---|---|---|
| 108 | 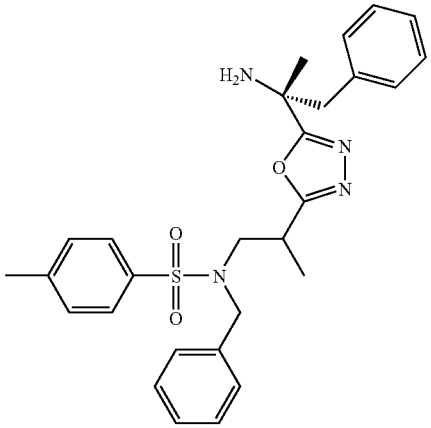 | 505 |

The following abbreviations are used throughout the text:

| Me: | methyl |
| Bu: | butyl |
| i-Bu: | isobutyl |
| t-Bu: | tert butyl |
| Et: | ethyl |
| Pr: | propyl |
| i-Pr: | isopropyl |
| Ar: | aryl |
| Ph: | phenyl |
| Ac: | acetyl |
| HOAt: | 1-hydroxy-7-azabenzotriazole |
| DMF: | N,N'-dimethyl formamide |
| DMSO: | dimethylsulfoxide |
| EDTA: | ethylene diamine tetraacetic acid |
| EDC: | 1-Ethyl-3-(3-dimethylaminopropyl)-carbodiimide |
| Boc: | tert-butyloxy carbonyl |
| CHAPS: | 3[(3-cholamidopropyl)dimethylammonio]-2-hydroxy-1-propanesulfonate |
| TFA: | trifluoroacetic acid |
| aq: | aqueous |
| rt: | room temperature |
| HPLC: | high performance liquid chromatography |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:

1. A compound of formula (I):

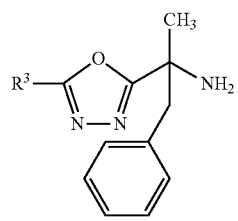

(I)

$R^3$ is selected from the group consisting of
- (1) —$C_{0-3}$ alkylene-$C_{6-10}$ aryl,
- (2) —$C_{0-3}$ alkylene-heteroaryl,
- (3) —$C_{0-3}$ alkylene-N-carbocyclic group, said N-carbocyclic group having from 3 to 12 ring carbon atoms and optionally having one ring double bond, wherein one or more of the ring carbon atoms may be replaced with an N, O or S atom, or a —NH—, —(C=O)— or —$SO_2$— group, said N-carbocyclic group optionally fused to a $C_{6-10}$ aryl,
- (4) —$C_{0-3}$ alkylene-C-carbocyclic group, said C-carbocyclic group having from 3 to 12 ring carbon atoms and optionally having one ring double bond, wherein one or more of the ring carbon atoms may be replaced with an N, O or S atom, or a —NH—, —(C=O)— or —$SO_2$— group, said C-carbocyclic group optionally fused to a $C_{6-10}$ aryl,
- (5) —$C_{0-3}$ alkylene-$Q^4$-$C_{1-10}$ alkyl,
- (6) —$C_{0-3}$ alkylene-$Q^4$-$C_{2-10}$ alkenyl,
- (7) —$C_{0-3}$ alkylene-$Q^4$-$C_{2-10}$ alkynyl, or
- (8) —$C_{0-3}$ alkylene-$Q^4$-$C_{0-3}$ alkylene-$C_{6-10}$ aryl,
  wherein said $R^3$ alkyl, alkylene, alkenyl, alkynyl, N-carbocyclic, C-carbocyclic, aryl and heteroaryl moieties are unsubstituted or substituted with one or more
  - (a) halo,
  - (b) —OH,
  - (c) —CN,
  - (d) —$NO_2$,
  - (e) —$C_{1-10}$ alkyl, (f) —O—C$_{1-10}$ alkyl,
(g) —C$_{3-12}$ cycloalkyl,
(h) —C$_{0-3}$ alkylene-C$_{6-10}$ aryl,
(i) —O—C$_{0-3}$ alkylene-C$_{6-10}$ aryl,
(j) —C(=O)—(O)$_m$—C$_{1-10}$ alkyl,
(k) —C(=O)—(O)$_m$—C$_{0-3}$ alkylene —C$_{6-10}$ aryl,
(l) —S(=O)$_2$—C$_{1-10}$ alkyl,
(m) —S(=O)$_2$—C$_{0-3}$ alkylene-C$_{6-10}$ aryl,
(n) —C$_{5-10}$ heteroaryl,
(o) —C(=O)—C$_{1-10}$ alkyl,
(p) —C$_{0-3}$ alkylene-N-carbocyclic group, said N-carbocyclic group having from to 12 ring carbon atoms and optionally having one ring double bond, wherein one or more of the ring carbon atoms may be replaced with an N, O or S atom, or a —NH—, —(C=O)— or —SO$_2$— group, said N-carbocyclic group optionally fused to a C$_{6-10}$ aryl,
(q) —C$_{0-3}$ alkylene-C-carbocyclic group, said C-carbocyclic group having from 3 to 12 ring carbon atoms and optionally having one ring double bond, wherein one or more of the ring carbon atoms may be replaced with an N, O or S atom, or a —NH—, —(C=O)— or —SO$_2$— group, said C-carbocyclic group optionally fused to a C$_{6-10}$ aryl,
(r) —(C=O)—OH,
(s) —C$_{0-3}$ alkylene-(Q$^2$)$_m$—NR$^c$R$^d$, wherein R$^c$ and R$^d$ are selected from the group consisting of
(i) hydrogen,
(ii) C$_{1-10}$ alkyl, and
(iii) C$_{0-6}$ alkylene-C$_{6-10}$ aryl,
or R$^c$ and R$^d$ are linked together with the N atom to form a carbocyclic group having four or five ring carbon atoms, wherein one or more of the ring carbon atoms may be replaced with an N, O or S atom, or a —(C=O)— or —SO$_2$— group,
and said alkyl, alkylene, cycloalkyl, C-carbocyclic, N-carbocyclic, aryl or heteroaryl moiety above is unsubstituted or substituted with one or more
(i) halo,
(ii) —OH,
(iii) —CN,
(iv) —C$_{1-10}$ alkyl,
(v) —C$_{2-10}$ alkenyl,
(vi) —C$_{2-10}$ alkynyl,
(vii) —O—C$_{1-10}$ alkyl,
(viii) —C$_{3-12}$ cycloalkyl,
(ix) —C$_{0-3}$ alkylene-C$_{6-10}$ aryl,
(x) —C(=O)—(O)$_m$—C$_{1-10}$ alkyl, or
(xi) —C(=O)—(O)$_m$—C$_{0-3}$ alkylene-C$_{6-10}$ aryl;
and Q$^2$, Q$^3$ and Q$^4$ are selected from the group consisting of
(a) —S(=O)$_n$—,
(b) —S—,
(c) —O—,
(d) —NR$^e$—
(e) —NR$^e$—S(=O)$_n$—,
(f) —NR$^e$—C(=O)—(O)$_m$—
(g) —C(=O)—(O)$_m$—
(h) —O—C(=O)—, and (i) 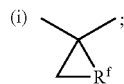;

wherein R$^e$ is selected from the group consisting of
(i) hydrogen,
(ii) —C$_{1-10}$ alkyl,
(iii) —C$_{0-3}$ alkylene-C$_{6-10}$ aryl,
(iv) heteroaryl
(v) —C$_{0-3}$ alkylene-Q$^3$-C$_{1-10}$ alkyl,
(vi) —C$_{0-3}$ alkylene-Q$^3$-C$_{2-10}$ alkenyl,
(vii) —C$_{0-3}$ alkylene-Q$^3$-C$_{2-10}$ alkynyl, or
(viii) —C$_{0-3}$ alkylene-Q$^3$-C$_{0-3}$ alkyl-C$_{6-10}$ aryl,
and R$^f$ is a one to four cyclic carbon chain, wherein one or more of the cyclic carbon atoms may be replaced with an N, O or S atom, or a —(C=O) or SO$_2$ group;

m is 0 or 1, n is 1 or 2, and pharmaceutically acceptable salts thereof, and individual enantiomers and diastereomers thereof.

2. The compound of claim 1, wherein R$^3$ is selected from the group consisting of
(1) —C$_{0-3}$ alkylene-C$_{6-10}$ aryl,
(2) —C$_{0-3}$ alkylene-heteroaryl,
(3) —C$_{0-3}$ alkylene-N-carbocyclic group, and
(4) —C$_{0-3}$ alkylene-C-carbocyclic group.

3. The compound of claim 1, which is a compound of formula (II')

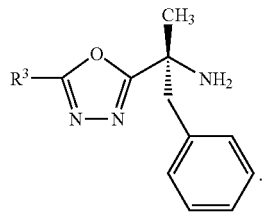

4. The compound of claim 1, wherein R$^3$ is selected from the group consisting of —C$_{0-3}$ alkylene-C$_{6-10}$ aryl and —C$_{0-3}$ alkylene-heteroaryl, wherein said heteroaryl has from 5 to 10 ring atoms.

5. The compound of claim 1 which is selected from the group consisting of:

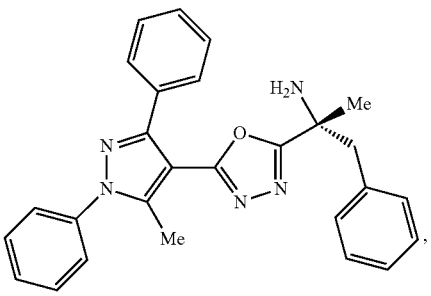

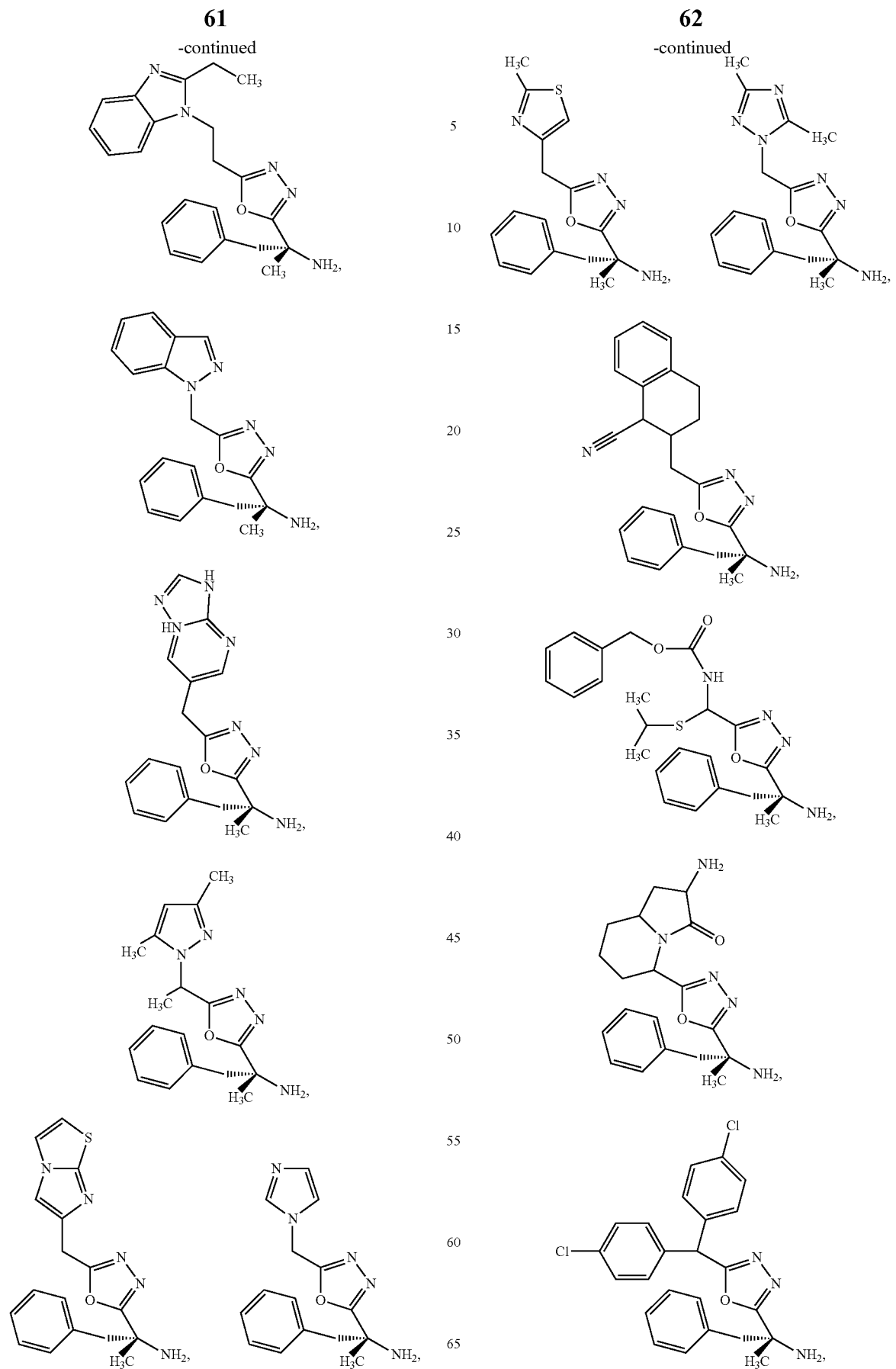

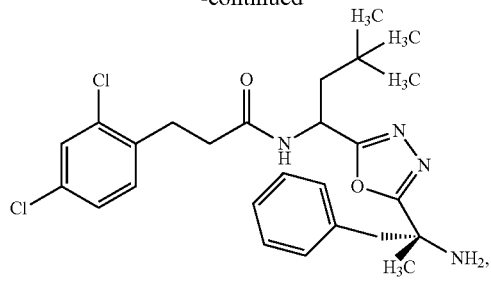
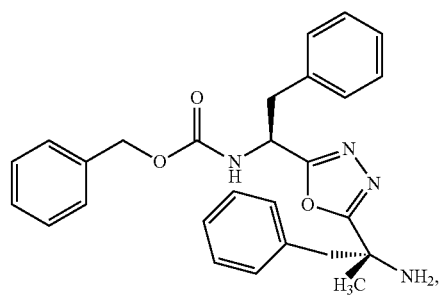
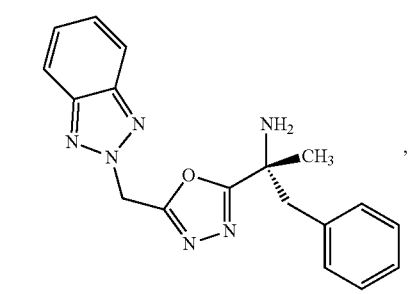
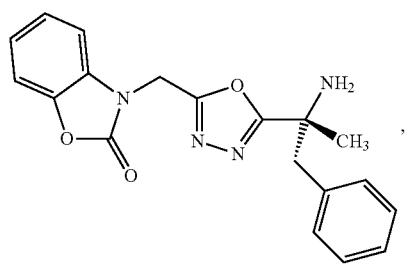
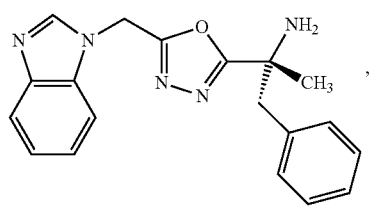
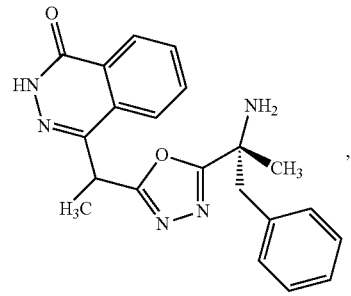
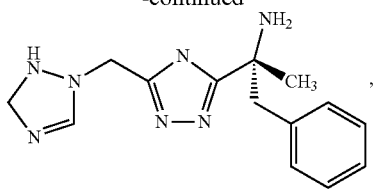
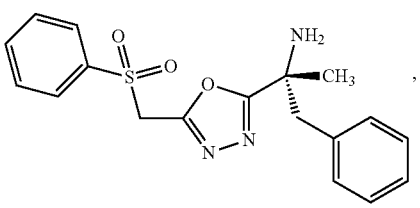
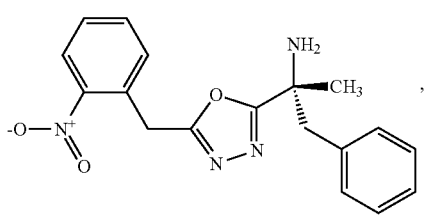
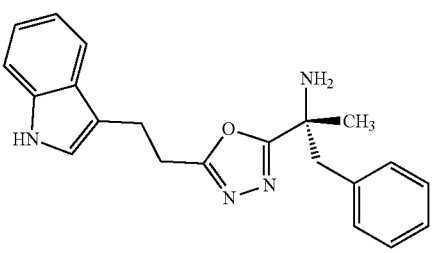
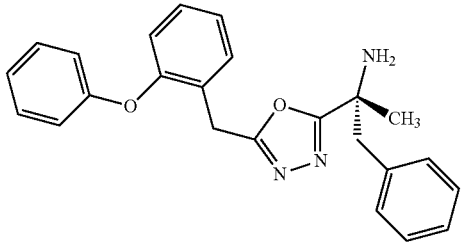
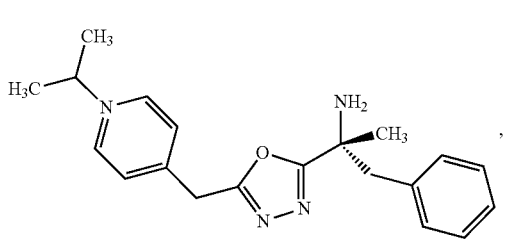

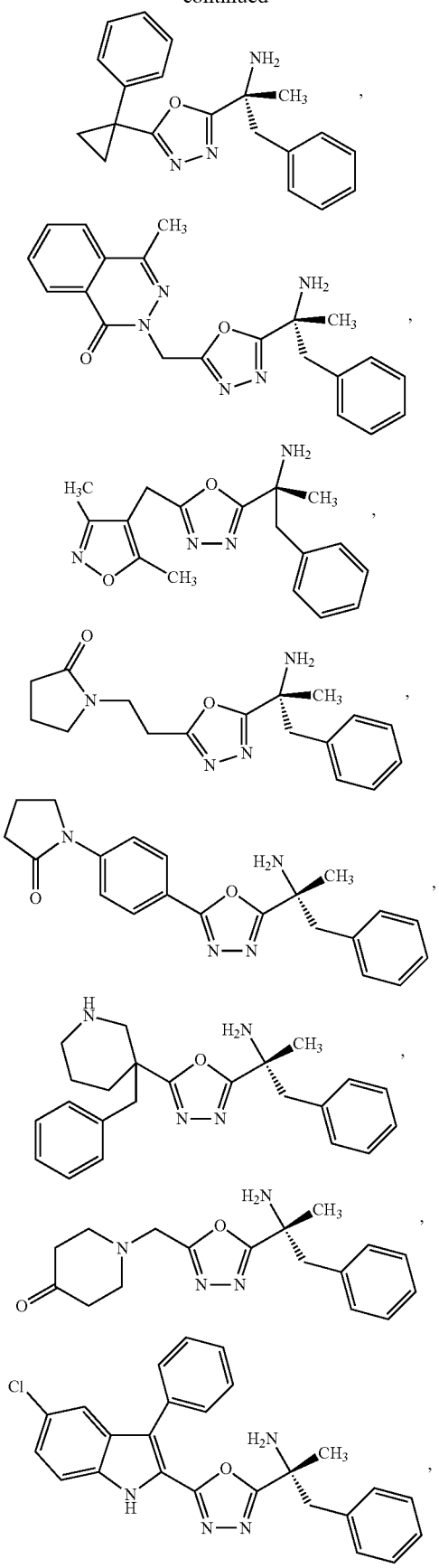
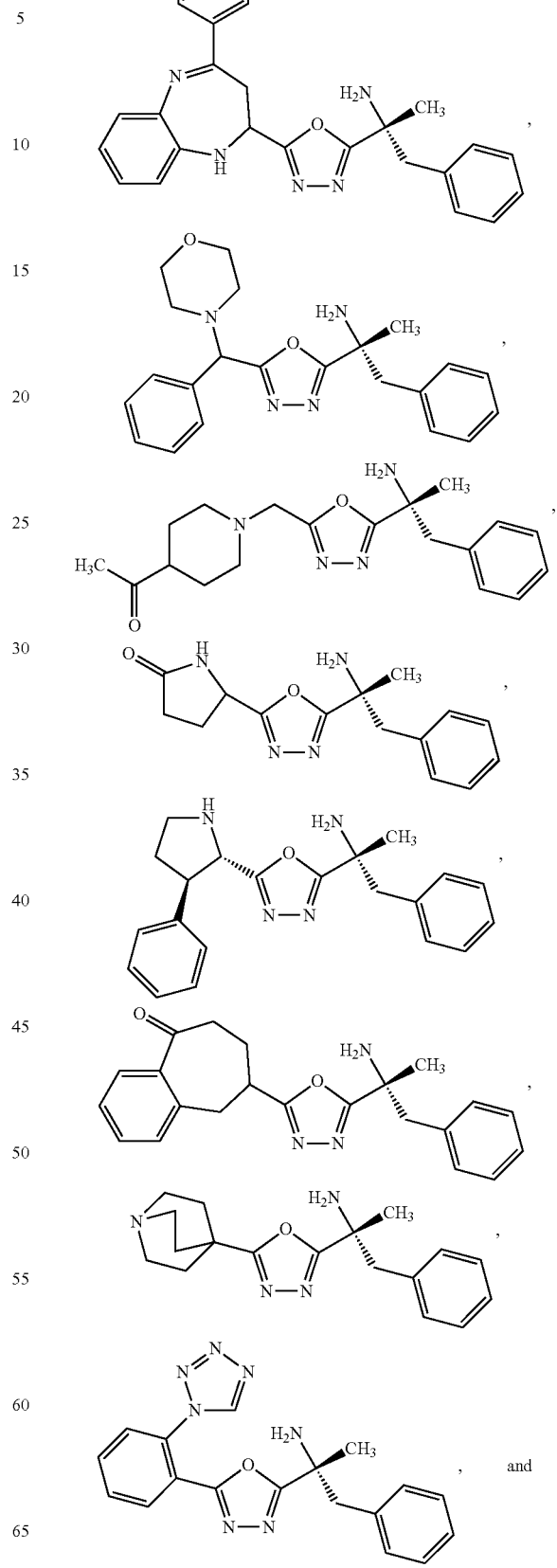

-continued
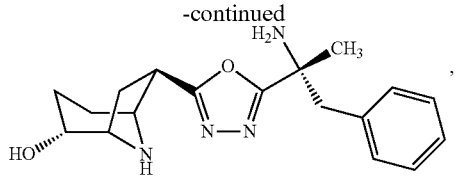
or a pharmaceutically acceptable salt thereof.
6. The compound of claim 1 which is selected from the group consisting of:
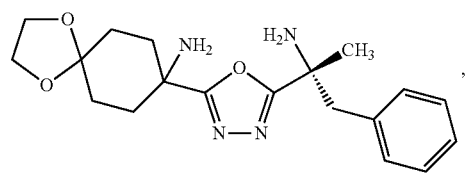
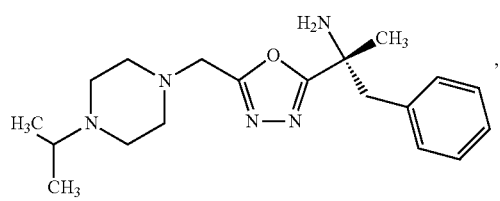
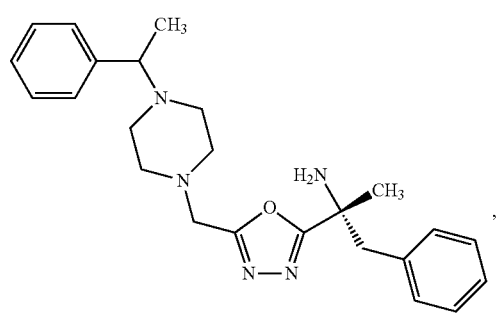
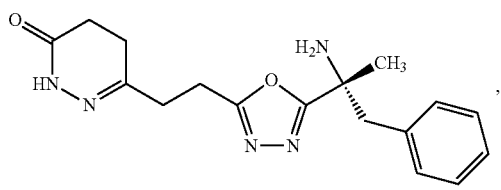
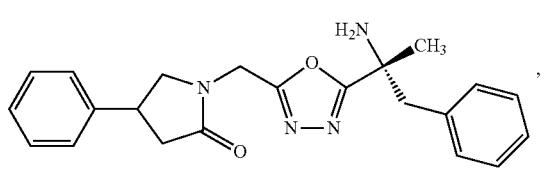
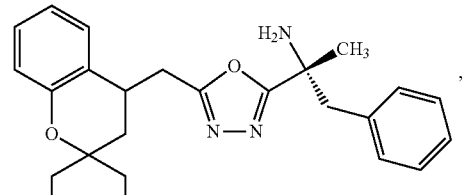
-continued
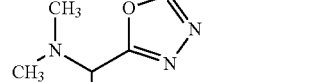
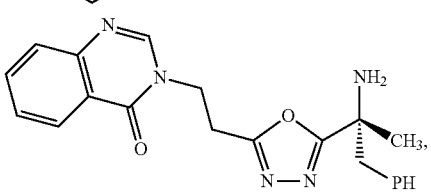
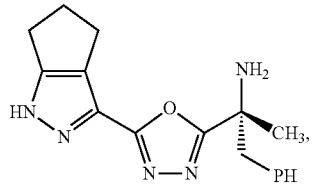
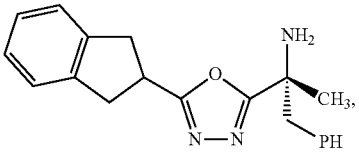
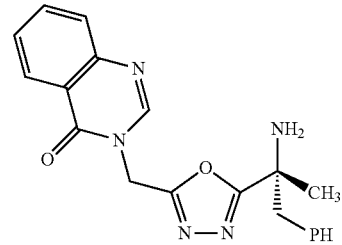
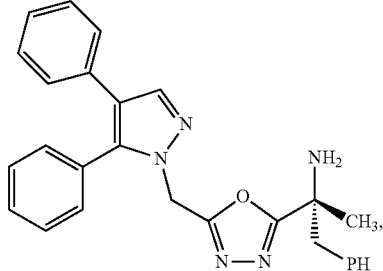
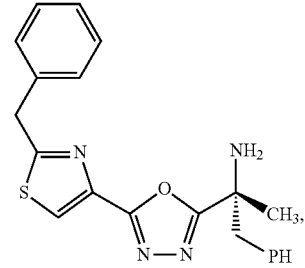

-continued
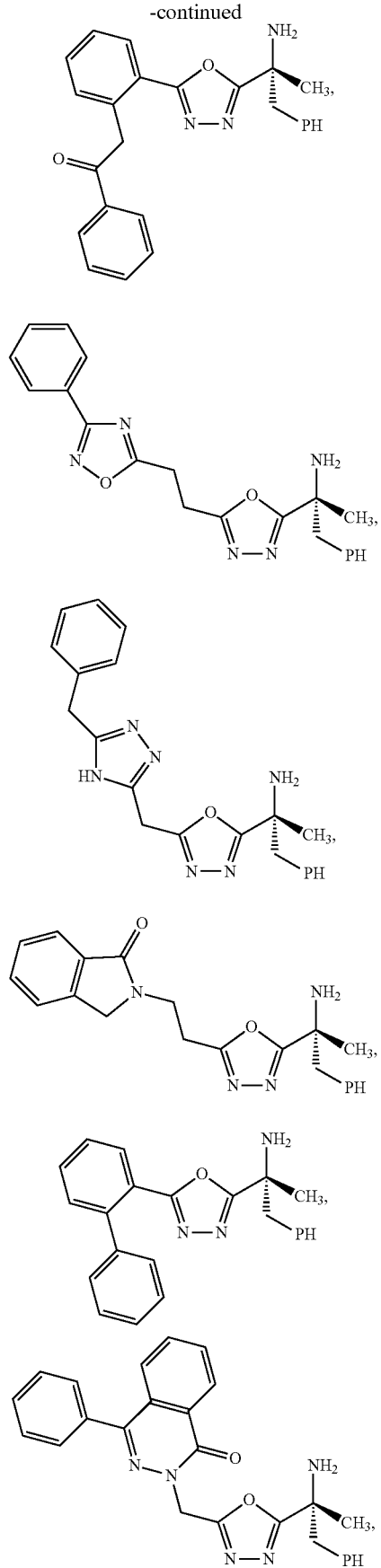
-continued
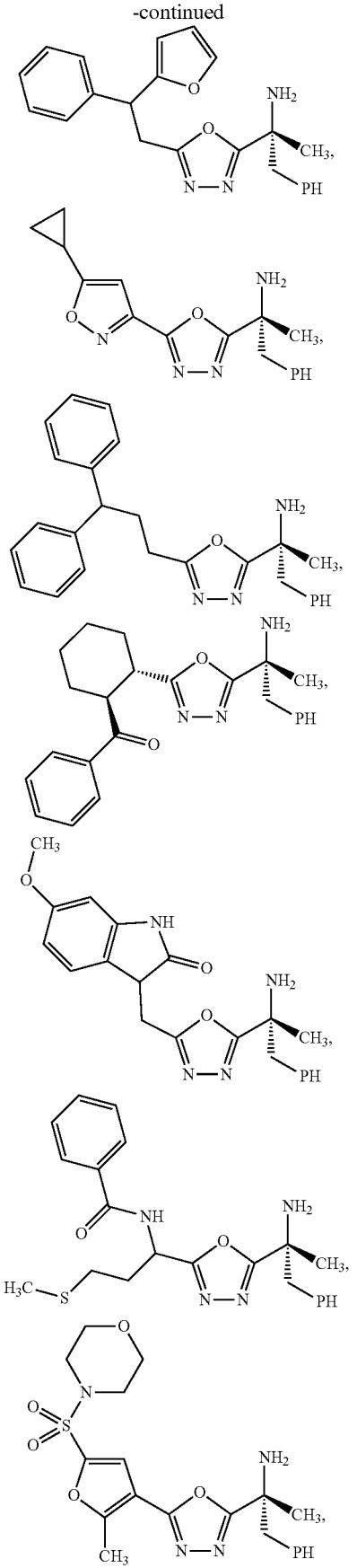

71
-continued
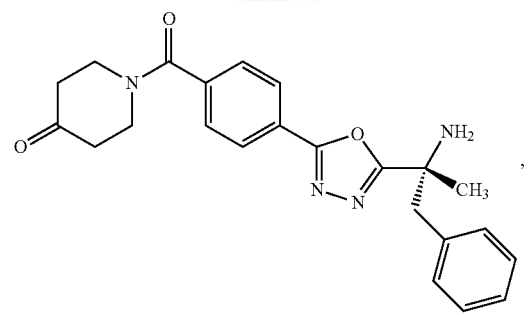
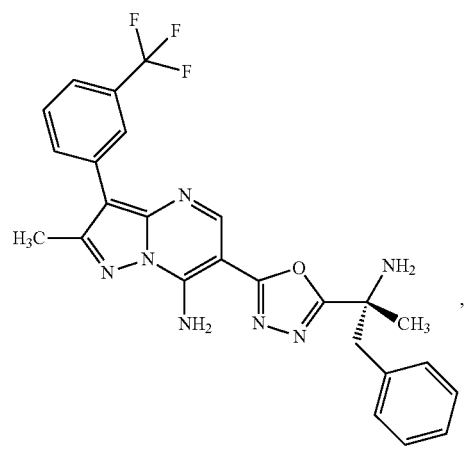
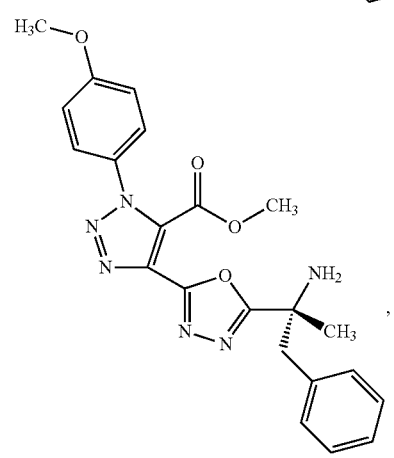
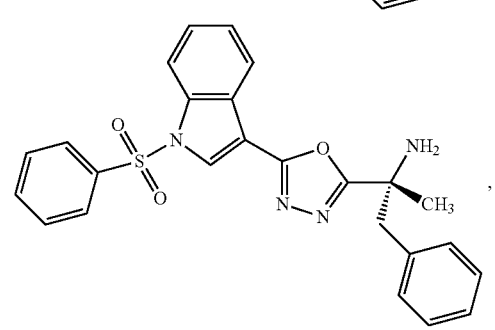
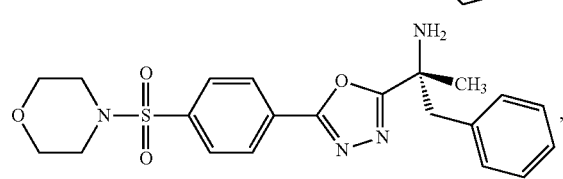
72
-continued
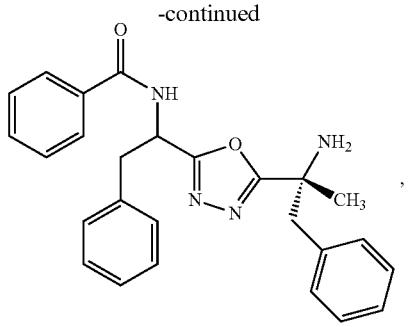
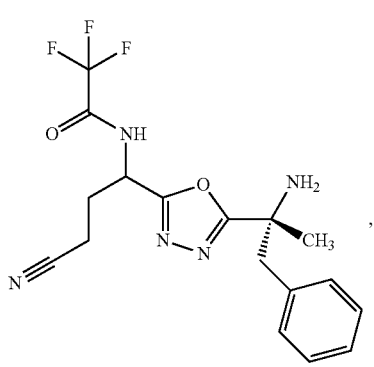
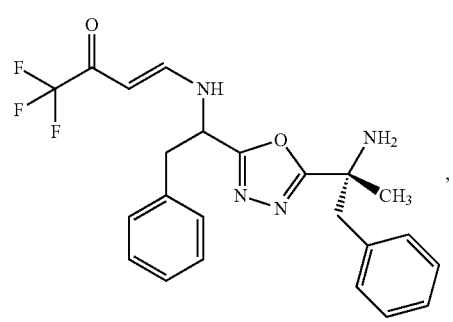
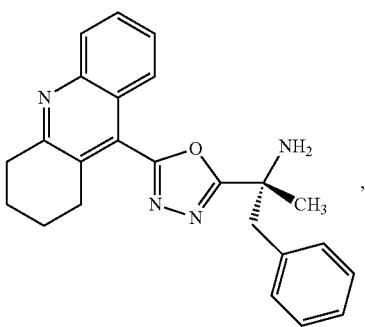
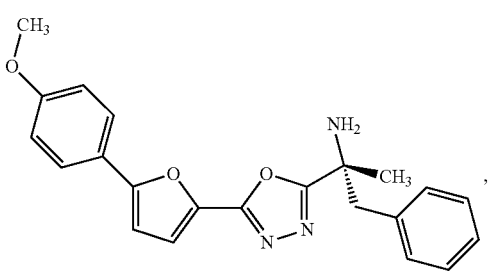
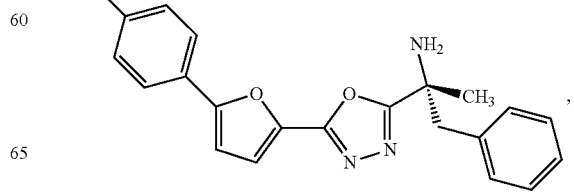

73
-continued
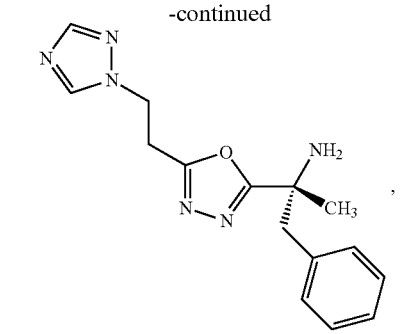
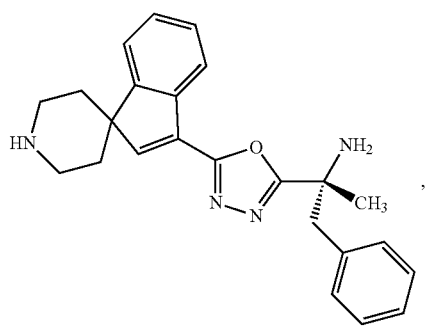
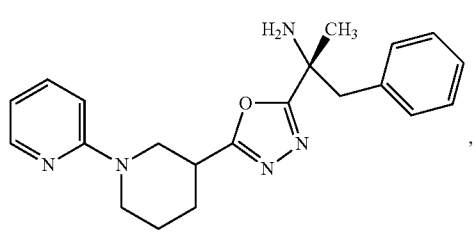
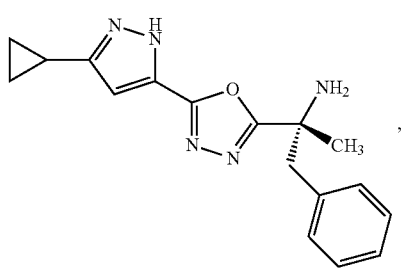
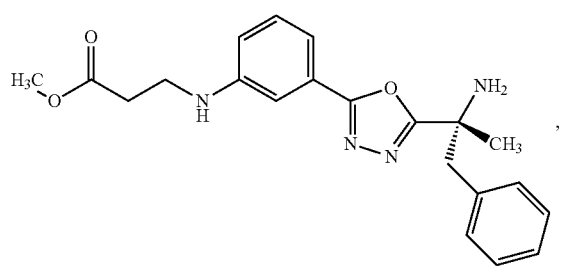
74
-continued
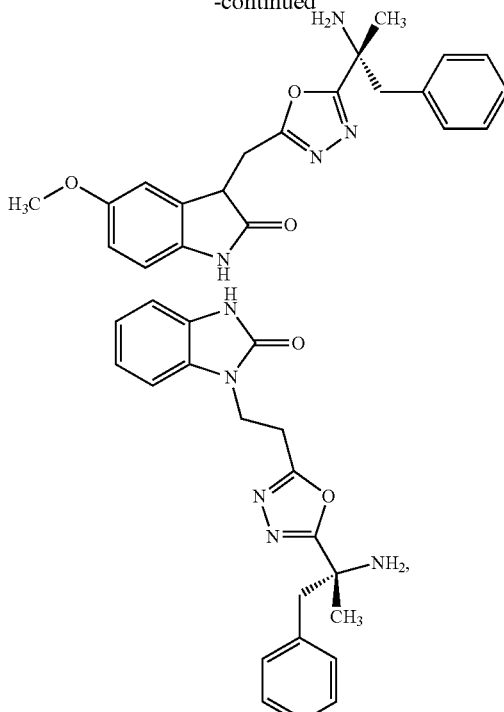
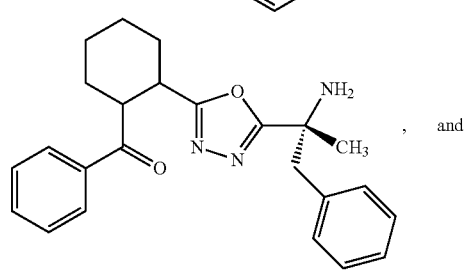
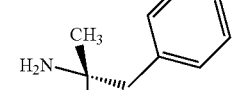
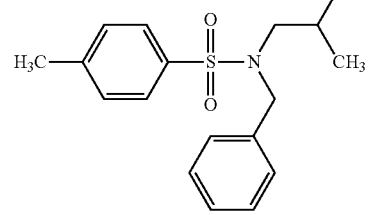
or a pharmaceutically acceptable salt thereof.
7. A pharmaceutical composition comprising a therapeutically effective amount of a compound of claim 1 or a pharmaceutically acceptable salt thereof and a pharmaceutically acceptable carrier.
* * * * *